(12) United States Patent
Kondo

(10) Patent No.: US 9,645,118 B2
(45) Date of Patent: May 9, 2017

(54) ULTRASONIC IMAGING APPARATUS AND ULTRASONIC IMAGING METHOD

(75) Inventor: Yuji Kondo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1534 days.

(21) Appl. No.: 12/409,723

(22) Filed: Mar. 24, 2009

(65) Prior Publication Data

US 2009/0241673 A1 Oct. 1, 2009

(30) Foreign Application Priority Data

Mar. 31, 2008 (JP) ................................. 2008-093211

(51) Int. Cl.
| | |
|---|---|
| A61B 6/00 | (2006.01) |
| G01N 29/06 | (2006.01) |
| A61B 8/08 | (2006.01) |
| A61B 8/14 | (2006.01) |
| G01S 7/52 | (2006.01) |

(Continued)

(52) U.S. Cl.
CPC ........... *G01N 29/0672* (2013.01); *A61B 8/14* (2013.01); *A61B 8/5207* (2013.01); *G01S 7/52025* (2013.01); *G01S 7/52046* (2013.01); *G01S 15/8915* (2013.01); *G10K 11/346* (2013.01);

(Continued)

(58) Field of Classification Search
USPC ................................................. 600/437–457
See application file for complete search history.

(56) References Cited

U.S. PATENT DOCUMENTS

| | | | | |
|---|---|---|---|---|
| 4,612,937 | A | * | 9/1986 | Miller ........................... 600/441 |
| 5,031,625 | A | * | 7/1991 | Higashiizumi et al. ...... 600/437 |

(Continued)

FOREIGN PATENT DOCUMENTS

| | | |
|---|---|---|
| JP | 7318635 A | 12/1995 |
| JP | 11-89846 A | 4/1999 |

(Continued)

OTHER PUBLICATIONS

English translation of JP (2005-342140).*

(Continued)

*Primary Examiner* — Amanda Lauritzen Moher
*Assistant Examiner* — Shahdeep Mohammed
(74) *Attorney, Agent, or Firm* — Sughrue Mion, PLLC

(57) ABSTRACT

An ultrasonic imaging apparatus in which ultrasonic tomographic images can be obtained without repeating ultrasonic transmission/reception at many times while sequentially changing the direction of the ultrasonic beam. The ultrasonic imaging apparatus includes: a transmitting and receiving unit for processing reception signals outputted from ultrasonic transducers; a sampling unit for generating a reception signal matrix representing ultrasonic echoes from sampling points on a section of the object; a conversion matrix calculating unit for calculating a conversion matrix representing weighting information when ultrasonic echoes from plural locations on the section are synthesized; an inverse matrix calculating unit for calculating an inverse matrix of the conversion matrix; and a sound source information calculating unit for calculating a product of the inverse matrix and the reception signal matrix to obtain a sound source signal matrix representing information on reflective sound sources within the object, and generating an image signal.

14 Claims, 18 Drawing Sheets

(51) Int. Cl.
*G01S 15/89* (2006.01)
*G10K 11/34* (2006.01)

(52) U.S. Cl.
CPC ...... *A61B 8/5215* (2013.01); *G01N 2291/044* (2013.01); *G01N 2291/106* (2013.01)

(56) References Cited

U.S. PATENT DOCUMENTS

| | | | | |
|---|---|---|---|---|
| 5,579,010 | A | * 11/1996 | Iihoshi et al. | 342/70 |
| 5,851,187 | A | * 12/1998 | Thomas et al. | 600/447 |
| 6,056,694 | A | * 5/2000 | Watanabe | G01S 7/02 600/447 |
| 6,685,645 | B1 | 2/2004 | McLaughlin et al. | |
| 2002/0156374 | A1* | 10/2002 | Miwa et al. | 600/437 |
| 2003/0045794 | A1* | 3/2003 | Bae | 600/437 |
| 2004/0193052 | A1* | 9/2004 | Ogawa | 600/440 |
| 2005/0197573 | A1* | 9/2005 | Roth et al. | 600/437 |

FOREIGN PATENT DOCUMENTS

| | | |
|---|---|---|
| JP | 20028004 A | 1/2002 |
| JP | 2003180688 A | 7/2003 |
| JP | 2005342140 A | 12/2005 |

OTHER PUBLICATIONS

English translation of JP (09-061409).*
English translation of JP (11-089846).*
Japanese Office Action corresponding to Japanese Patent Application No. 2008-093211, dated Apr. 3, 2012.

* cited by examiner

VIBRATORS

VIBRATORS

ULTRASONIC IMAGING APPARATUS AND ULTRASONIC IMAGING METHOD

BACKGROUND OF THE INVENTION

Field of the Invention

The present invention relates to an ultrasonic imaging apparatus and an ultrasonic imaging method for performing diagnosis of organs in a living body or nondestructive inspection by transmitting and receiving ultrasonic waves.

Description of a Related Art

Generally, in an ultrasonic imaging apparatus, an ultrasonic probe including plural ultrasonic transducers having functions of transmitting and receiving ultrasonic waves is used. When an ultrasonic beam formed by synthesizing plural ultrasonic waves is transmitted from the ultrasonic probe toward an object to be inspected, the ultrasonic beam is reflected in a region having different acoustic impedances, that is, a boundary between tissues within the object. Thus generated ultrasonic echoes are received and images are formed based on the intensity of the ultrasonic echoes, and thereby, the status within the object can be reproduced on a display screen.

In a conventional ultrasonic imaging apparatus, there is used a method of obtaining information on the entire region of interest by estimating reflection signal information on an ultrasonic beam based on ultrasonic echoes obtained by the reflection of the ultrasonic beam formed within the object, and sequentially changing the direction of the ultrasonic beam. In order to display this in a typical monitor, so-called scan conversion is performed.

FIG. 20 is a diagram for explanation of transmission beam forming. In a method called electronic scan, a group of arranged vibrators are used. When high-frequency voltages (drive signals) are applied to the respective vibrators included in the group of vibrators, ultrasonic waves are introduced into the object. At this time, as shown in FIG. 20, since the times when the respective vibrators are driven are varied, lags are caused in ultrasonic waves to be introduced into the object. When the respective vibrators are sufficiently small, the ultrasonic waves generated by the respective vibrators spherically propagate within the living body, and regions where phases of ultrasonic waves match one another and the ultrasonic waves are mutually intensified are formed because of the lags.

As shown in FIG. 20, when a focal point is formed in a certain position, the transmission times may be adjusted such that the wavefronts from the respective vibrators are located on concentric circles around the point. In the focal position, the phases of the ultrasonic waves transmitted from all vibrators match one another, and the ultrasonic waves are mutually most intensified. Similarly, in another position, ultrasonic waves from part of vibrators are intensified. Alternatively, in other positions, regions where ultrasonic waves are mutually weakened due to phase reversal are formed. As a result, so-called side lobes are formed. As described above, not only an ultrasonic acoustic field having a beam-like form exists, but also some acoustic fields are formed in the all regions.

FIG. 21 is a diagram for explanation of reception beam forming. The mechanism of reception beam forming is the same as that of the transmission beam forming. At reception of ultrasonic echoes, it is assumed that ultrasonic echoes are reflected by a reflector and spherically spread from the reflector. Accordingly, also at the reception, the reception signals from the reflector are mutually most intensified by providing the same delays as those at transmission to the reception signals outputted from the plural vibrators and adding those reception signals to one another.

Here, at the same times when ultrasonic echoes from the reflector reach the respective vibrators, if ultrasonic echoes from another sound source reach the vibrators, the ultrasonic echoes from the other sound source are also mutually intensified. That is, what are included in the added reception signals are not necessarily the ultrasonic echoes only from the reflector of interest, and the ultrasonic echoes from the other sound source become noise. When the transmission ultrasonic beams exist only on the straight line connecting the vibrator and the reflector, this noise does not exist. However, in the conventional transmission system as described above, it is impossible to form such a transmission ultrasonic beam, and mixture of noise due to acoustic fields is not avoidable.

In FIGS. 20 and 21, the ultrasonic beams in a direction orthogonal to the vibrator surfaces are shown, however, when the vibrators are sufficiently small as described above, the transmitted ultrasonic waves spread as a point sound source in all directions, and further, ultrasonic echoes from all directions can be received at reception. As shown in FIG. 22, when the amounts of delay are increased to be asymmetric at the right and left sides (vertically in the drawing), an ultrasonic beam can be tilted. FIG. 22 shows reception, but the same is true at transmission. Generally, in a method called sector scan, this transmission and reception method is used with extremely small vibrator widths.

Although the acoustic fields are formed in the all regions as described above, the ultrasonic beam transmitted and received is narrow, the reception signals mainly obtained represent information from a limited region on the ultrasonic beam. Accordingly, in order to obtain tomographic images, the ultrasonic beam should be sequentially focused on the entire region of interest, and a method of shifting the ultrasonic beam is adopted.

FIG. 23 shows shifting of an ultrasonic beam in the case of linear scan. As shown in FIG. 23, the ultrasonic beam is shifted by changing the groups of vibrators that contribute to transmission and reception. However, according to the method, spacings of the ultrasonic beams are equal to the spacings of the vibrators and the resolving power of tomographic images depends on the beam spacings, and therefore, the obtained image resolving power is not sufficient. Accordingly, various methods are devised in order to obtain more ultrasonic beams. FIG. 24 shows an example, called a micro-angle method. According to the micro-angle method, the symmetry in amounts of delay is eliminated even using the same group of vibrators, and thereby, beams slightly different in directions can be obtained. Further, in the case of sector scan, a method of changing the direction of the beam by changing the amounts of delay in FIG. 22 is adopted.

The information on the ultrasonic beam obtained in this manner is directly depicted on an X-Y monitor in an early ultrasonic imaging apparatus. However, in view of data recording or the like, the information is currently depicted on a common monitor by using a method of scan conversion.

FIG. 25 shows an example of scan conversion in the case of linear scan. In the scan conversion in the case of linear scan, the processing of converting data on points indicated by diamond marks in ultrasonic beam coordinates into data on point (X,Y) indicated by a circle in X-Y coordinates on a monitor is performed. FIG. 26 shows an example of scan conversion in the case of sector scan. In the scan conversion in the case of sector scan, the processing of converting data on points indicated by diamond marks in ultrasonic beam coordinates into data on point $(r, \phi)$ indicated by a circle in polar coordinates, that is, on point (X,Y) indicated by a circle in X-Y coordinates on a monitor is performed.

When a micro region is seen, if the number of data of ultrasonic beams is larger than the number of data in X-Y coordinates, thinning of the data is necessary. On the other hand, if the number of data of ultrasonic beams is smaller than the number of data in X-Y coordinates, addition for the lack of data is necessary. Here, improper thinning causes aliasing. Further, in addition of data, the lack of data is created by interpolation processing from the data of surrounding ultrasonic beam has been mainly adopted, but the interpolation processing is one kind of image processing and just the estimation of unknown information based on surrounding information.

As described above, in the conventional ultrasonic imaging apparatus, it has been necessary to repeat transmission and reception of ultrasonic waves in various beam directions at many times to obtain tomographic images. Further, the scan conversion processing does not necessarily reproduce precisely the reflective sound source information of the living body, but means for obtaining good image quality by a kind of artificial processing. Furthermore, the configuration of the ultrasonic beam depends on the geometric relationship, and thereby, there is a disadvantage that the images to be obtained may differ depending on the setting of the sound speed within the living body.

As a related conventional technology, in U.S. Pat. No. 6,685,645 discloses systems and methods of obtaining an image using a broad beam at one ultrasonic transmission. However, in U.S. Pat. No. 6,685,645, a specific method of estimating tomographic images is necessarily not disclosed.

Further, Japanese Patent Application Publication JP-A-11-89846 discloses an ultrasonic imaging apparatus intended for higher image quality by improving the S/N ratio. In the ultrasonic imaging apparatus, reception signals are converted into complex signals by orthogonal detector, filtering is performed on the real parts and imaginary parts, amplitudes are calculated based on the real parts and the imaginary parts, and images are displayed based on the amplitudes. However, in order to obtain the reception signals, plural times of ultrasonic transmission and reception are executed with respect to one direction.

SUMMARY OF THE INVENTION

The present invention has been achieved in view of the above-mentioned points. A purpose of the present invention is to provide an ultrasonic imaging apparatus and an ultrasonic imaging method in which ultrasonic tomographic images can be obtained without repeating ultrasonic transmission and reception at many times while sequentially changing the direction of the ultrasonic beam.

In order to accomplish the purpose, an ultrasonic imaging apparatus according to one aspect of the present invention includes: a transmitting and receiving unit for supplying at least one drive signal to at least one ultrasonic transducer to transmit ultrasonic waves to an object to be inspected, and processing reception signals outputted from plural ultrasonic transducers that have received ultrasonic echoes from the object; a sampling unit for sampling the reception signals processed by the transmitting and receiving unit to generate a reception signal matrix representing ultrasonic echoes from plural sampling points on a section of the object; conversion matrix calculating means for calculating a conversion matrix representing weighting information when ultrasonic echoes from plural locations on the section of the object are synthesized; inverse matrix calculating means for calculating an inverse matrix of the conversion matrix calculated by the conversion matrix calculating means; and sound source information calculating means for calculating a product of the inverse matrix calculated by the inverse matrix calculating means and the reception signal matrix generated by the sampling unit to obtain a sound source signal matrix representing information on reflective sound sources within the object, and generating an image signal representing an ultrasonic image within the object, based on the sound source signal matrix.

Further, an ultrasonic imaging method according to one aspect of the present invention includes the steps of: (a) calculating a conversion matrix representing weighting information when ultrasonic echoes from plural locations on a section of an object to be inspected are synthesized; (b) calculating an inverse matrix of the conversion matrix calculated at step (a); (c) supplying at least one drive signal to at least one ultrasonic transducer to transmit ultrasonic waves to the object, and processing reception signals outputted from plural ultrasonic transducers that have received ultrasonic echoes from the object; (d) sampling the reception signals processed at step (c) to generate a reception signal matrix representing ultrasonic echoes from plural sampling points on the section of the object; and (e) calculating a product of the inverse matrix calculated at step (b) and the reception signal matrix generated at step (d) to obtain a sound source signal matrix representing information on reflective sound sources within the object, and generating an image signal representing an ultrasonic image within the object, based on the sound source signal matrix.

According to the present invention, the product of the inverse matrix of the conversion matrix representing weighting information when ultrasonic echoes from plural locations on the section of the object are synthesized and the reception signal matrix representing ultrasonic echoes from plural sampling points on the section of the object is calculated, and thereby, the sound source signal matrix representing information on reflective sound sources within the object is obtained, and an image signal representing an ultrasonic image within the object are generated based on the sound source signal matrix. Therefore, ultrasonic tomographic images can be obtained without repeating ultrasonic transmission and reception at many times while sequentially changing the direction of the ultrasonic beam.

DESCRIPTION OF THE PREFERRED EMBODIMENTS

Figure 1:
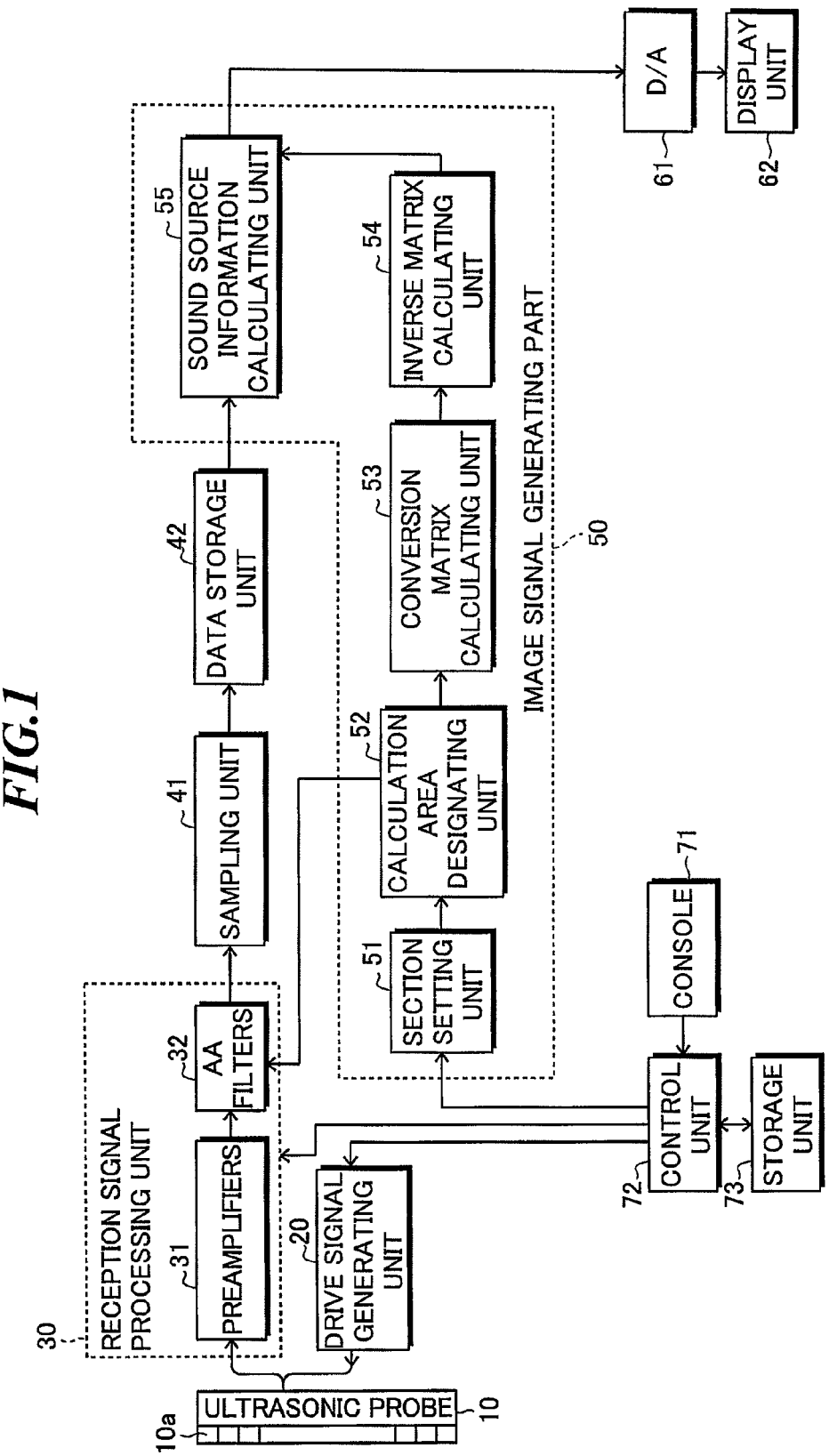
FIG. 1 is a block diagram showing a configuration of an ultrasonic imaging apparatus according to the first embodiment of the present invention.

Hereinafter, embodiments of the present invention will be explained in detail with reference to the drawings. The same reference numerals are assigned to the same components with and the explanation thereof will be omitted.

FIG. 1 is a block diagram showing a configuration of an ultrasonic imaging apparatus according to the first embodiment of the present invention. The ultrasonic imaging apparatus has an ultrasonic probe 10, a drive signal generating unit 20, a reception signal processing unit 30, a sampling unit 41, a data storage unit 42, an image signal generating part 50, a D/A converter 61, a display unit 62, a console 71, a control unit 72, and a storage unit 73. Here, the drive signal generating unit 20 and the reception signal processing unit 30 form a transmitting and receiving unit.

The ultrasonic probe 10 includes plural ultrasonic transducers 10a forming a one-dimensional transducer array. The respective ultrasonic transducers 10a transmit ultrasonic beams based on applied drive signals, and receive propagating ultrasonic echoes and output reception signals.

Each ultrasonic transducer includes a vibrator having electrodes formed on both ends of a material having a piezoelectric property (piezoelectric material) such as a piezoelectric ceramics represented by PZT (Pb (lead) zirconate titanate), a polymeric piezoelectric element represented by PVDF (polyvinylidene difluoride), or the like. When a pulsed or continuous wave electric signal is applied to the electrodes of the vibrator, the piezoelectric material expands and contracts. Further, the respective vibrators expand and contract by receiving the propagating ultrasonic waves to generate electric signals. These electric signals are outputted as reception signals of ultrasonic waves.

The drive signal generating unit 20 includes plural pulsers corresponding to the plural ultrasonic transducers 10a, for example. The drive signal generating unit 20 supplies one or plural drive signals for driving one or plural ultrasonic transducers to the ultrasonic probe 10, or adjusts amounts of delay of the drive signals based on the transmission delay pattern selected by the control unit 72 and supply the drive signals to the ultrasonic probe 10 such that the ultrasonic waves transmitted from the plural ultrasonic transducers 10a form a predetermined wavefront or an ultrasonic beam.

The reception signal processing unit 30 includes plural preamplifiers 31 and plural AA (anti-aliasing) filters 32 corresponding to the plural ultrasonic transducers 10a. The reception signals outputted from the ultrasonic transducers 10a are amplified in the amplifiers 31. Further, although not shown in the drawing, the reception signals are converted into their envelope information by envelope detection processing. The AA filters 32 perform filter processing on the reception signals outputted from the amplifiers 31 for preventing aliasing in sampling.

The sampling unit 41 samples and A/D-converts the reception signals outputted from the reception signal processing unit 30, and thereby, generates a reception signal matrix (reception data) representing ultrasonic echoes from m×n sampling points on a section of an object to be inspected. For example, the sampling unit 41 two-dimensionally samples the reception signals processed by the reception signal processing unit 30 by using the depth direction on the section of the object as a first coordinate axis and the arrangement direction of the plural ultrasonic transducers 10a as a second coordinate axis.

The sampling frequency at this time is lower than the frequency normally specified in the sampling theorem. Accordingly, as explained above, the AA filters 32 for preventing aliasing are necessary. The filter setting in the AA filters 32 follows the sampling frequency and depends on the designation of the calculation area (m×n sampling points) on the section to be computed. The reception data sampled by the sampling unit 41 is temporarily stored in the data storage unit 42 configured by a hard disk, memory, or the like.

The image signal generating part 50 includes a section setting unit 51, a calculation area designating unit 52, a conversion matrix calculating unit 53, an inverse matrix calculating unit 54, and a sound source information calculating unit 55. The section setting unit 51 sets a section of the object to be displayed in an ultrasonic image, under the control of the control unit 72. The calculation area designating unit 52 designates a calculation area (m×n sampling points) on the section set by the section setting unit 51.

When the calculation area is designated, the conversion matrix calculating unit 53 calculates a conversion matrix representing weighting information for synthesis of ultrasonic echoes from plural positions on the section of the object. For example, the conversion matrix calculating unit 53 calculates a conversion matrix representing weighting information for synthesis of ultrasonic echoes from plural positions two-dimensionally located on the section of the object by using the depth direction on the section of the object as the first coordinate axis and the direction orthogonal to the first coordinate axis within the section of the object as the second coordinate axis. The inverse matrix calculating unit 54 calculates an inverse matrix of the conversion matrix calculated by the conversion matrix calculating unit 53.

The sound source information calculating unit 55 calculates a product of the inverse matrix of the conversion matrix calculated by the inverse matrix calculating unit 54 and the reception signal matrix generated by the sampling unit 41 and stored in the data storage unit 42, and thereby, obtains a sound source signal matrix representing information on reflective sound sources within the object and generates an image signal representing an ultrasonic image within the object based on the sound source signal matrix.

The D/A converter 61 converts the digital image signal outputted from the image signal generating part 50 into an analog image signal. The display unit 62 includes a display device such as CRT or LCD, for example, and displays a diagnostic image based on the analog image signal.

The control unit 72 controls the drive signal generating unit 20, the reception signal processing unit 30, the image signal generating part 50, and so on according to the operation of an operator using the console 71. The image signal generating part 50 and the control unit 72 can be realized by a CPU and software (programs). The software (programs) is stored in the storage unit 73. As a recording medium in the storage unit 73, not only a built-in hard disk but also a flexible disk, MO, MT, RAM, CD-ROM, DVD-ROM, or the like may be used. The image signal generating part 50 may be configured by a digital circuit.

Next, a principle of operation of the ultrasonic imaging apparatus shown in FIG. 1 will be explained in detail.

The present invention is not to scan-convert the reception signals as in the related art, but to estimate tomographic information by a completely different computing method. The ultrasonic waves transmitted to the object are reflected by a so-called acoustic boundary surface on which the characteristic acoustic impedance changes within the object. According to the acoustic theory, when the reflection source is a mirror boundary, sound is reflected at the same reflection angle as the incident angle. That is, for reflection of sound in the transmission direction, the reflection surface should exists perpendicularly to the ultrasonic beam.

However, since the reflection source in the living body, for example, is sufficiently smaller than the wavelength of ultrasonic waves, sound is scattered and reflected in all directions. The fact that tomographic images can be constructed while narrow ultrasonic beams are transmitted and ultrasonic echoes from the beam directions are obtained as reception waves as in the related art is an undeniable evidence based thereon. If it is true, the reflection signals from the reflection sources should be nearly equally returned to all of the arranged vibrators. The present invention is based on the idea that the reception signal received by one vibrator is the sum of reflection signals from all locations within the section of the object.

That is, the present invention is to obtain tomographic information regardless of ultrasonic acoustic fields without assuming that the reception signals are on the transmitted ultrasonic beams. It is assumed that the ultrasonic echoes from the reflection sources within the object are returned to the vibrators as ultrasonic waves from point sound sources. It is assumed that the ultrasonic echoes received by one vibrator are reflected from all regions within the section to be obtained, and that the reflection sources at the same distance from the vibrator contribute to the reception signal at a specific time. Accordingly, simultaneous linear equations having variables of reflective sound source information within the section can be set up based on the reception signals obtained from the plural vibrators, and tomographic images can be obtained by solving the simultaneous linear equations. According to the method, tomographic images can be obtained by one transmission and reception if the sufficient broad acoustic field is provided. Further, it is unnecessary to set the sound speed for the estimation of sound source information although the hypothesis that the sound speed within the living body is homogeneous remains necessary.

Figure 2:
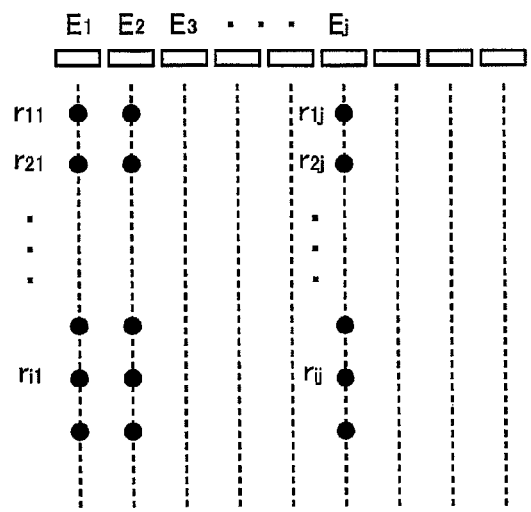
FIG. 2 shows positional relationships between a group of arranged vibrators and ultrasonic reflection sources within the object.

FIG. 2 shows positional relationships between a group of arranged vibrators and ultrasonic reflection sources within the object. Here, it is assumed that a finite number of ultrasonic reflection sources exist within the object in correspondence with the individual vibrators included in the group of arranged vibrators. As shown in FIG. 2, a reception signal based on ultrasonic echoes from an ultrasonic reflection source at the i-th depth (hereinafter, also referred to as "depth i") in the j-th vibrator (hereinafter, also referred to as "vibrator j") is referred to as $r_{ij}$.

Using part or all of the arranged vibrators, pulsed ultrasonic waves are transmitted into the object. As is in the case of the conventional method, ultrasonic echoes are received in a period from the transmission of pulsed ultrasonic waves to the next transmission of pulsed ultrasonic waves. At a given time, the transmission acoustic field forms wavefront within a tomographic surface. When the wavefront reaches the ultrasonic reflection source within the tomographic surface, reflection waves toward the vibrators are generated from the ultrasonic reflection source as a sound source. Assuming that the tomographic surface is expressed by the x-y plane, the sound source signal in a certain location within the tomographic surface is referred to as $s_{yx}$.

Figure 3:
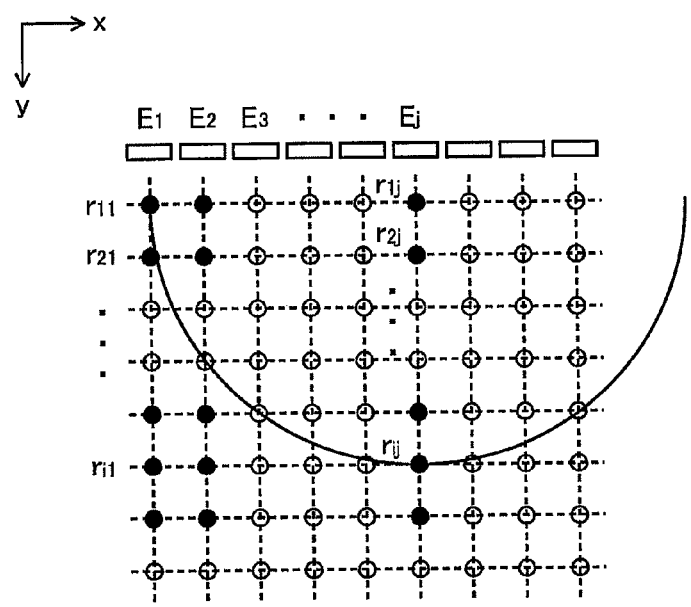
FIG. 3 shows a coordinate system of the tomographic surface and a coordinate system of the reception signal in the same coordinate system.

FIG. 3 shows the coordinate system of the tomographic surface and the coordinate system of the reception signal in the same coordinate system. Assuming that x, y take discrete values, in FIG. 3, for intuitive and easy understanding, the depth "y" corresponds to the row and the lateral distance "x" corresponds to the column.

Assuming that the sound source signal $s_{yx}$ has a point sound source property and the reflected sound spreads in all directions, it is considered that all of the sound source signals on the section reach the j-th vibrator. The reception signal $r_{ij}$ is a reception signal at a specific time, and reaches the vibrator j at time 2i/c if the sound speed "c" of the acoustic field is constant. This is a reflection signal from a specific depth, and sound sources at a distance equal to the depth i from the vibrator j contribute to the signal reaching the vibrator j at the time regardless of the speed of sound. Accordingly, weighting of $a_{yx}$ is respectively provided to the sound source signal $s_{yx}$, and $a_{yx}=0$ for the sound sources not at the same distance from the vibrator j as that of the reception signal $r_{ij}$. Note that $a_{yx}$ is weighting information depending on i, j, and this is newly expressed as $a_{ij-yx}$.

Here, a matrix having "m" rows and "n" columns is considered as sound source signals. This is equal to that the spatial resolving power of the section to be obtained is set to "m" in the depth direction and "n" in the lateral direction. In FIG. 3, the coordinates of the tomographic surface and the coordinates of the reception signal by the vibrator are the same. The reception signal $r_{ij}$ is the sum of $s_{yx}$ on the arc shown in FIG. 3 as expressed in the following equation (1).

$$r_{ij} = \sum_{x=1}^{n} \sum_{y=1}^{m} (a_{ij-yx} \cdot s_{yx}) \quad (1)$$

Note that the following conditions are obtained because only the sound sources located at an equal distance contribute to the reception signal at a certain time.

If $(j-x)^2+y^2=i^2, a_{ij-yx}=1$

If $(j-x)^2+y^2\neq i^2, a_{ij-yx}=0$ (2)

The equation (1) is developed and expressed by matrices, and the following equation (3) is obtained.

$$r_{ij} = \begin{pmatrix} a_{ij-11} & a_{ij-12} & \cdots & a_{ij-1n} & a_{ij-21} & a_{ij-22} & \cdots & a_{ij-2n} & \cdots & a_{ij-mn} \end{pmatrix} \begin{pmatrix} s_{11} \\ s_{12} \\ \vdots \\ s_{1n} \\ s_{21} \\ s_{22} \\ \vdots \\ s_{2n} \\ \vdots \\ s_{mn} \end{pmatrix} \quad (3)$$

In the case where the positions of the vibrators and reception signals are the same as positions of sound sources, $i_{max}=m$, $j_{max}=n$. Accordingly, when matrices with respect to all reception signals are obtained from the equation (3), the following equation (4) is obtained.

$$\begin{pmatrix} r_{11} \\ r_{21} \\ \vdots \\ r_{m1} \\ r_{12} \\ r_{22} \\ \vdots \\ r_{m2} \\ \vdots \\ r_{1n} \\ r_{2n} \\ \vdots \\ r_{mn} \end{pmatrix} = \begin{pmatrix} a_{11-11} & a_{11-12} & \cdots & a_{11-1n} & a_{11-12} & a_{11-22} & \cdots & a_{11-2n} & \cdots & a_{11-m1} & a_{11-m2} & \cdots & a_{11-mn} \\ a_{21-11} & a_{21-12} & \cdots & a_{21-1n} & a_{21-12} & a_{21-22} & \cdots & a_{21-2n} & \cdots & a_{21-m1} & a_{21-m2} & \cdots & a_{21-mn} \\ \vdots & \vdots & \ddots & \vdots & \vdots & \vdots & \ddots & \vdots & \ddots & \vdots & \vdots & \ddots & \vdots \\ a_{m1-11} & a_{m1-12} & \cdots & a_{m1-1n} & a_{m1-12} & a_{m1-22} & \cdots & a_{m1-2n} & \cdots & a_{m1-m1} & a_{m1-m2} & \cdots & a_{m1-mn} \\ a_{12-11} & a_{12-12} & \cdots & a_{12-1n} & a_{12-12} & a_{12-22} & \cdots & a_{12-2n} & \cdots & a_{12-m1} & a_{12-m2} & \cdots & a_{12-mn} \\ a_{22-11} & a_{22-12} & \cdots & a_{22-1n} & a_{22-12} & a_{22-22} & \cdots & a_{22-2n} & \cdots & a_{22-m1} & a_{22-m2} & \cdots & a_{22-mn} \\ \vdots & \vdots & \ddots & \vdots & \vdots & \vdots & \ddots & \vdots & \ddots & \vdots & \vdots & \ddots & \vdots \\ a_{m2-11} & a_{m2-12} & \cdots & a_{m2-1n} & a_{m2-12} & a_{m2-22} & \cdots & a_{m2-2n} & \cdots & a_{m2-m1} & a_{m2-m2} & \cdots & a_{m2-mn} \\ \vdots & \vdots & \ddots & \vdots & \vdots & \vdots & \ddots & \vdots & \ddots & \vdots & \vdots & \ddots & \vdots \\ a_{1n-11} & a_{1n-12} & \cdots & a_{1n-1n} & a_{1n-12} & a_{1n-22} & \cdots & a_{1n-2n} & \cdots & a_{1n-m1} & a_{1n-m2} & \cdots & a_{1n-mn} \\ a_{2m-11} & a_{2m-12} & \cdots & a_{2m-1n} & a_{2m-12} & a_{2m-22} & \cdots & a_{2m-2n} & \cdots & a_{2m-m1} & a_{2m-m2} & \cdots & a_{2m-mn} \\ \vdots & \vdots & \ddots & \vdots & \vdots & \vdots & \ddots & \vdots & \ddots & \vdots & \vdots & \ddots & \vdots \\ a_{mn-11} & a_{mn-12} & \cdots & a_{mn-1n} & a_{mn-12} & a_{mn-22} & \cdots & a_{mn-2n} & \cdots & a_{mn-m1} & a_{mn-m2} & \cdots & a_{mn-mn} \end{pmatrix} \begin{pmatrix} s_{11} \\ s_{12} \\ \vdots \\ s_{1n} \\ s_{21} \\ s_{22} \\ \vdots \\ s_{2n} \\ \vdots \\ s_{m1} \\ s_{m2} \\ \vdots \\ s_{mn} \end{pmatrix} \quad (4)$$

The respective matrices are replaced by R, A, S, the following equation (5) is obtained.

$AS=R$ (5)

That is, the sound source signal matrix S is given by solving the simultaneous linear equations in the equation (4). The simultaneous linear equations can be solved by a method called sweep out or Gauss elimination method. Further, the conversion matrix A is a square matrix having a size of m×n, and inverse matrix $A^{-1}$ can be obtained. The sound source signal matrix S is given by the product of the inverse matrix $A^{-1}$ of the conversion matrix and the reception signal matrix R as expressed by the following equation (6).

$S=A^{-1}R$ (6)

Since the conversion matrix A is given only from the geometrical positional relationship as expressed by the equation (2), it can be calculated prior to the reception of signals. Accordingly, the inverse matrix $A^{-1}$ can be computed in advance, and the processing that should actually be performed in the reception period is multiplication of the matrices in the equation (6). Further, only the desired elements within the sound source signal matrix S can be computed.

Figure 4:
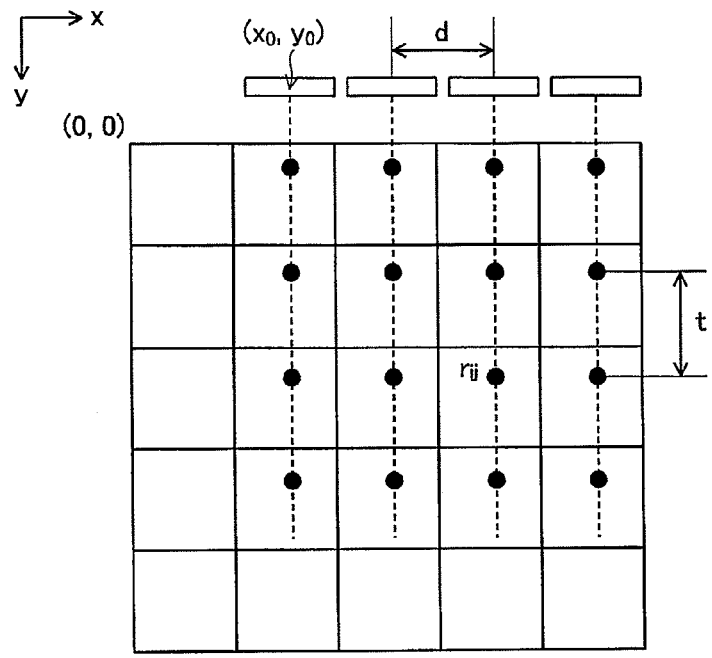
FIG. 4 shows the coordinate system of the tomographic surface and the coordinate system of the reception signal in the different coordinate systems.

FIG. 4 shows the coordinate system of the tomographic surface and the coordinate system of the reception signal in the different coordinate systems. Although the coordinate system of the tomographic surface to be obtained and the coordinate system of the reception signal are the same in FIG. 3, that is not an indispensable condition. As long as m×n simultaneous linear equations can be set up for the sound source signal matrix S having m×n variables, the coordinate setting as shown in FIG. 4, for example, may be used. In this case, the following equations may be used as conditions of the conversion matrix A.

If $(x_0+dj-x)^2+(y-y_0)^2=(ti)^2, a_{ij-yx}=1$

If $(x_0+dj-x)^2+(y-y_0)^2\neq(ti)^2, a_{ij-yx}=0$ (7)

That is, if the position at one end $(x_0, y_0)$ of the arranged vibrators in the section coordinates to be obtained and the distance "d" between vibrators are given, the conversion matrix A can be calculated. In the equations (7), "t" refers to a distance within the living body determined by the sampling interval, however, t=1 may be applied in the matrix calculation because "t" is necessary only for conversion of x, y into distances within the living body.

Figure 5:
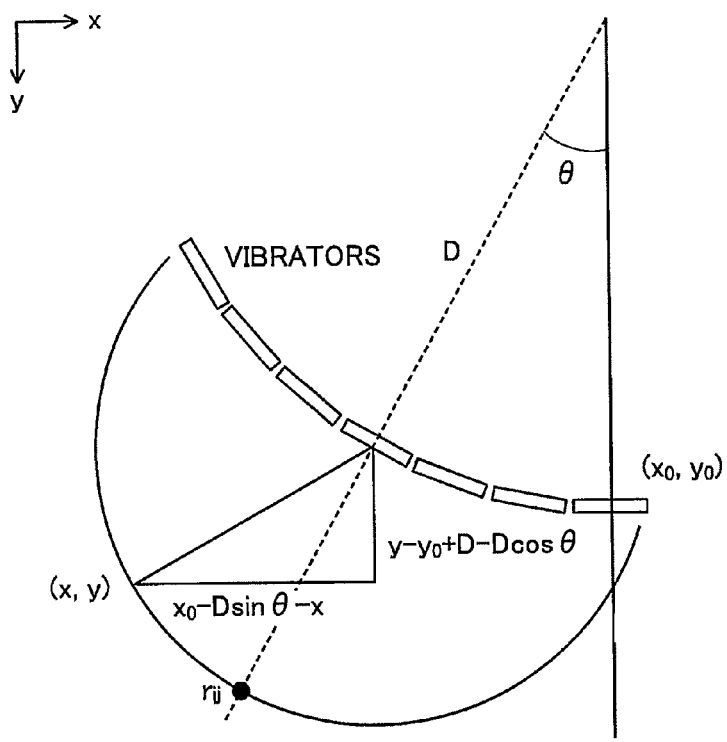
FIG. 5 is a diagram for explanation of a method of calculating a conversion matrix in the case of using a convex probe.

FIG. 5 is a diagram for explanation of a method of calculating a conversion matrix in the case of using a convex probe. When plural vibrators are arranged in a convex formation as in the convex probe, if the initial coordinates $(x_0, y_0)$ of the vibrator orthogonal to the y-axis of the section coordinates are given and the hypothetical distance of center D of the vibrator arrangement is given, conversion matrix A can be obtained according to the following equations (8).

If $(x_0-D \sin \theta-x)^2+(y-y_0+D-D \cos \theta)^2=(ti)^2, a_{ij-yx}=1$

If $(x_0-D \sin \theta-x)^2+(y-y_0+D-D \cos \theta)^2\neq(ti)^2, a_{ij-yx}=0$ (8)

where the following equation (9) holds with respect to the vibrator distance "d".

$\theta=j\cdot\sin^{-1}(d/D)$ (9)

Note that "j" is the order of arrangement from the vibrator located in $(x_0, y_0)$.

As described above, according to the present invention, all sound source information within the section can be obtained based on the reception signals obtained by one transmission and reception of all vibrators. That is, the transmitted ultrasonic acoustic field forms a continuous wavefront and the wavefront reaches all regions of interest within the object, then tomographic images can be obtained by one transmission and reception.

Next, the second embodiment of the present invention will be explained. In the second embodiment, weighting of matrix computation in consideration of the acoustic field is performed.

In general, unless a spherical wave acoustic field is formed in a homogeneous medium, the acoustic field intensity is not constant within the space. Further, the acoustic intensity becomes lower as sound propagates, and thus, the deeper the reflection position, the weaker the reflective sound source intensity. In view of the facts, assuming that the reflective sound source is weighted by the intensity "w" of the transmission acoustic field, $w_{ij-yx}$ may be used in place of $a_{ij-yx}$. Accordingly, the equations (2) can be replaced by the following equations (10).

If $(j-x)^2+y^2=i^2, a_{ij-yx}=w_{ij-yx}$

If $(j-x)^2+y^2\neq i^2, a_{ij-yx}=0$ (10)

Figure 6:
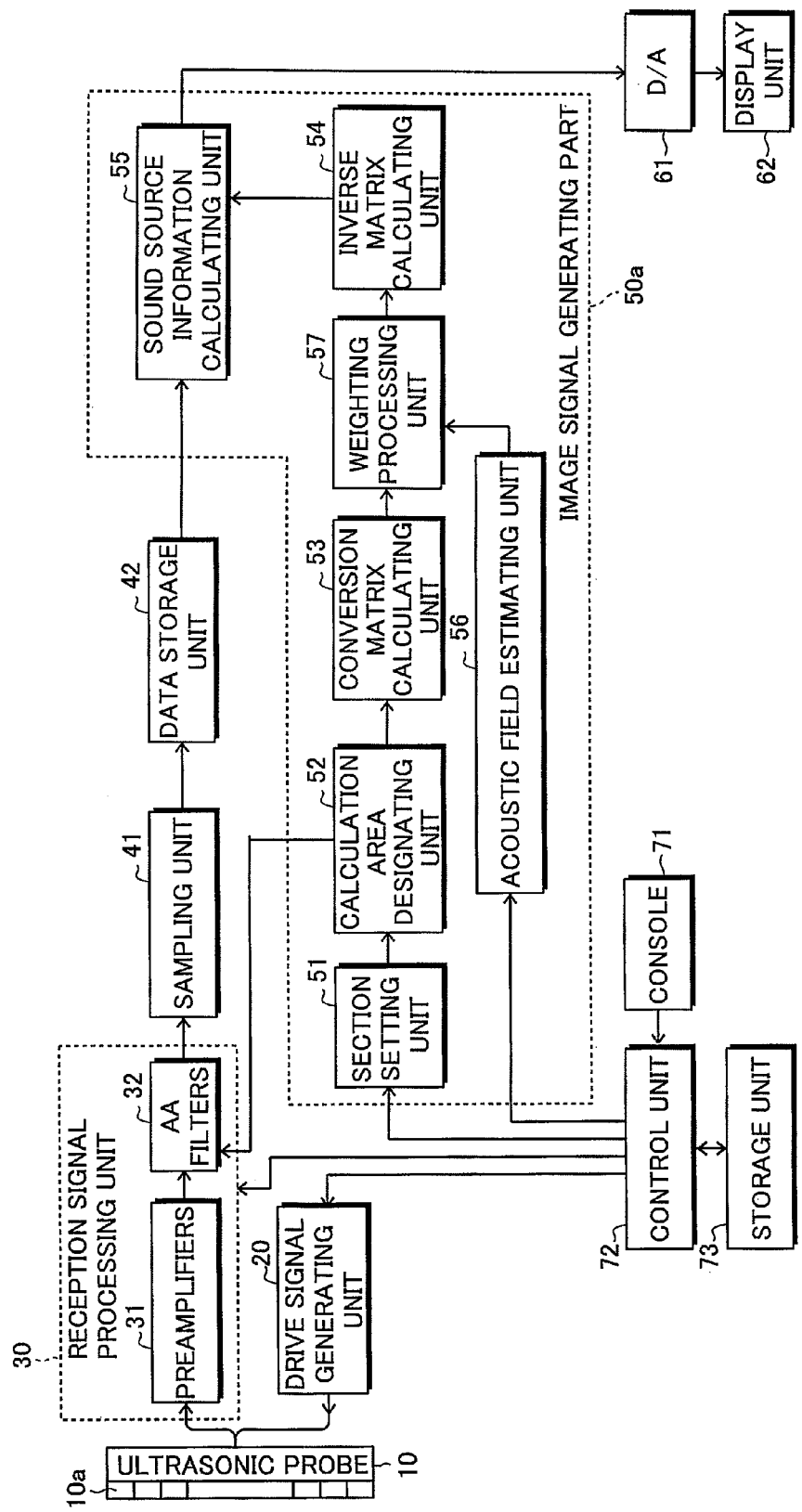
FIG. 6 is a block diagram showing a configuration of an ultrasonic imaging apparatus according to the second embodiment of the present invention.

FIG. 6 is a block diagram showing a configuration of an ultrasonic imaging apparatus according to the second embodiment of the present invention. In the second embodiment, in an image signal generating part 50a, an acoustic field estimating unit 56 and a weighting processing unit 57 are added to the first embodiment shown in FIG. 1. The acoustic field estimating unit 56 estimates an acoustic field based on the conditions set by the control unit 72. Further, the weighting processing unit 57 weights the respective elements included in the conversion matrix calculated by the conversion matrix calculating unit 53 based on the acoustic field estimation made by the acoustic field estimating unit 56. The inverse matrix calculating unit 54 calculates an inverse matrix of the conversion matrix weighting-processed by the weighting processing unit 57.

Next, the third embodiment of the present invention will be explained. In the third embodiment, matrix computation in a complex region is performed.

Figure 7:
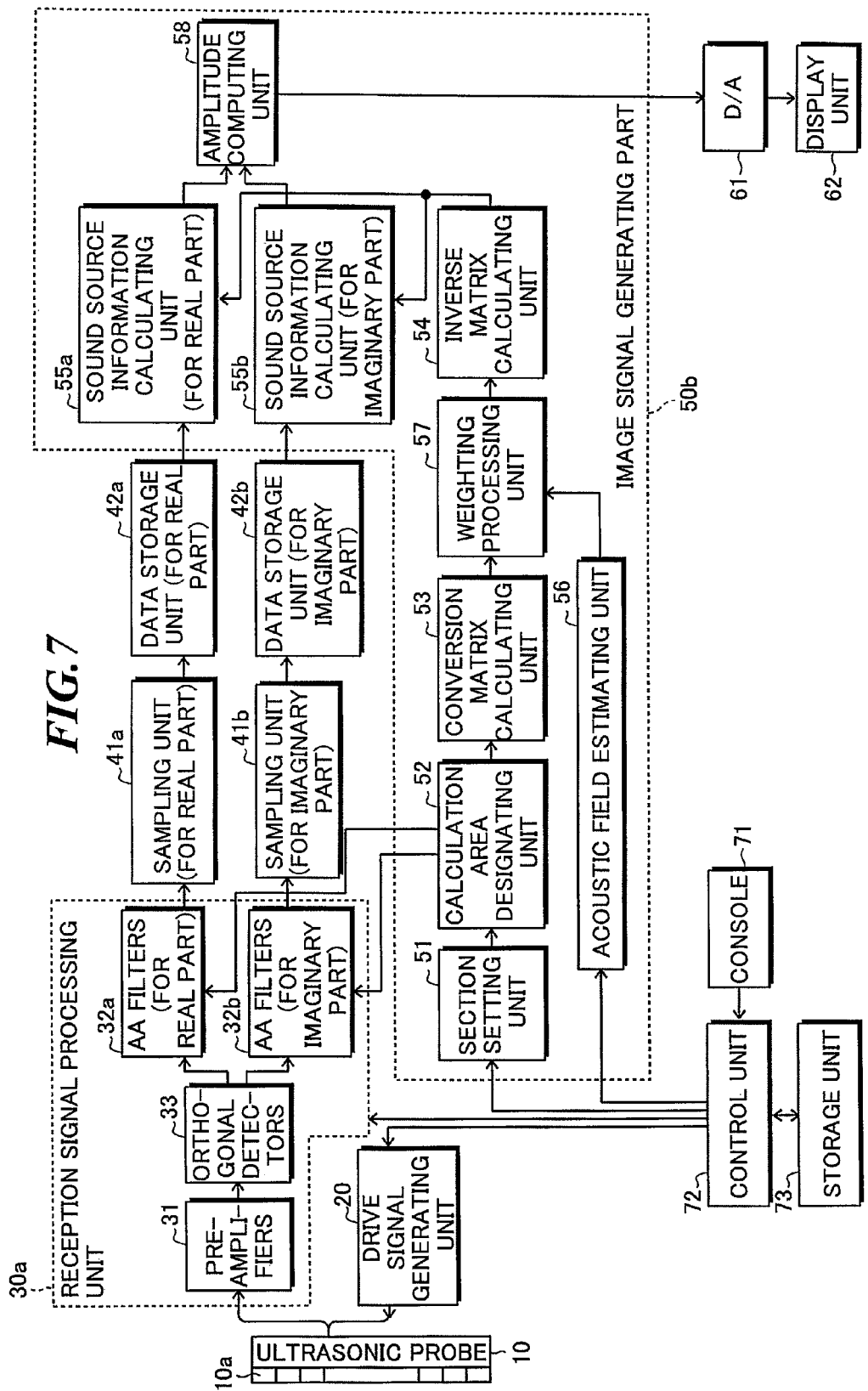
FIG. 7 is a block diagram showing a configuration of an ultrasonic imaging apparatus according to the third embodiment of the present invention.

FIG. 7 is a block diagram showing a configuration of an ultrasonic imaging apparatus according to the third embodiment of the present invention. As shown in FIG. 7, in a reception signal processing unit 30a, plural preamplifiers 31, orthogonal detectors 33 for converting the respective reception signals into signals at a baseband frequency and detecting real parts and imaginary pars, and a rear part AA filter 32a and an imaginary part AA filter 32b for the respective reception signals are provided corresponding to the plural ultrasonic transducers 10a.

Figure 8:
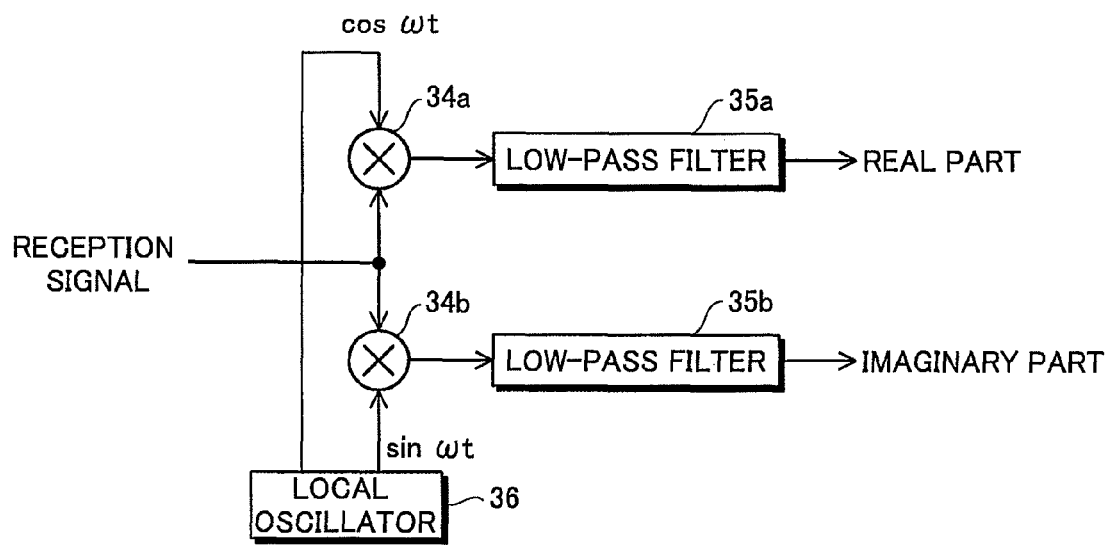
FIG. 8 shows a configuration example of an orthogonal detector.

FIG. 8 shows a configuration example of the orthogonal detector. The orthogonal detector includes multipliers 34a and 34b, low-pass filters 35a and 35b, and a local oscillator 36 for generating a first signal (cos ωt) and a second signal (sin ωt) having phases orthogonal to each other. The multiplier 34a obtains the real part of the reception signal (I-axis component) by multiplying the reception signal by the first signal (cos ωt) and the imaginary part of the reception signal (Q-axis component) by multiplying the reception signal by the second signal (sin ωt). The subsequent processing of the reception signal is performed on the real part and the imaginary part in the same manner. The low-pass filters 35a and 35b remove unwanted wideband components from the real part and the imaginary part of the reception signal, respectively.

Referring to FIG. 7 again, in the ultrasonic imaging apparatus, a sampling unit 41a for sampling the real parts of the reception signals outputted from the reception signal processing unit 30a and generating reception data of the real parts, a sampling unit 41b for sampling the imaginary parts of the reception signals outputted from the reception signal processing unit 30a and generating reception data of the imaginary parts, a data storage unit 42a for storing the reception data of the real parts, and a data storage unit 42b for storing the reception data of the imaginary parts are provided.

Further, in an image signal generating part 50b, a sound source information calculating unit 55a for calculating the real parts of the sound source signals based on the reception data of the real parts, a sound source information calculating unit 55b for calculating the imaginary parts of the sound source signals based on the reception data of the imaginary parts, and an amplitude computing unit 58 for obtaining amplitudes of the sound source signals based on the real parts and the imaginary parts of the sound source signals are provided.

The sound source information calculating unit 55a calculates a product of the inverse matrix calculated by the inverse matrix calculating unit 54 and the reception signal matrix generated by the sampling unit 41a and stored in the data storage unit 42a, and thereby, obtains a sound source signal matrix (real parts) representing information on reflective sound sources within the object. Further, the sound source information calculating unit 55b calculates a product of the inverse matrix calculated by the inverse matrix calculating unit 54 and the reception signal matrix generated by the sampling unit 41b and stored in the data storage unit 42b, and thereby, obtains a sound source signal matrix (imaginary parts) representing information on reflective sound sources within the object.

The amplitude computing unit 58 obtains amplitudes of the sound source signals by adding squares of the real parts of the sound source signals included in the sound source signal matrix (real parts) and the imaginary parts of the sound source signals included in the sound source signal matrix (imaginary parts) and calculating their square roots, and generates an image signal representing an ultrasonic image within the object based on the amplitudes.

According to the third embodiment, since the phase information of the reception signals is held by orthogonal detection of the reception signals and computation is performed with the reception signals as complex information, the S/N ratio can be improved for higher image quality. In FIG. 7, the acoustic field estimating unit 56 and the weighting processing unit 57 are provided as is the case of the second embodiment shown in FIG. 6, however, they are not necessarily provided as in the first embodiment shown in FIG. 1.

Next, the fourth embodiment of the present invention will be explained. In the fourth embodiment, a method of obtaining ultrasonic resolving power greater than the number of elements is used. The basic configuration of the ultrasonic imaging apparatus is the same as that of any one of the first to third embodiments.

What is necessary for calculation of sound source information is to set up a required number of simultaneous linear equations. That is, the same number of reception signals as the number (m×n) of section coordinate data to be obtained are required, and the calculation condition of the conversion matrix A is determined depending on the coordinate system of the reception signals, i.e., the shape and position of the probe. According to the idea, even if the number of vibrators is less than the azimuth resolving power (x direction), m×n sample data may be secured by shortening the sampling intervals of the reception signals.

Figure 9:
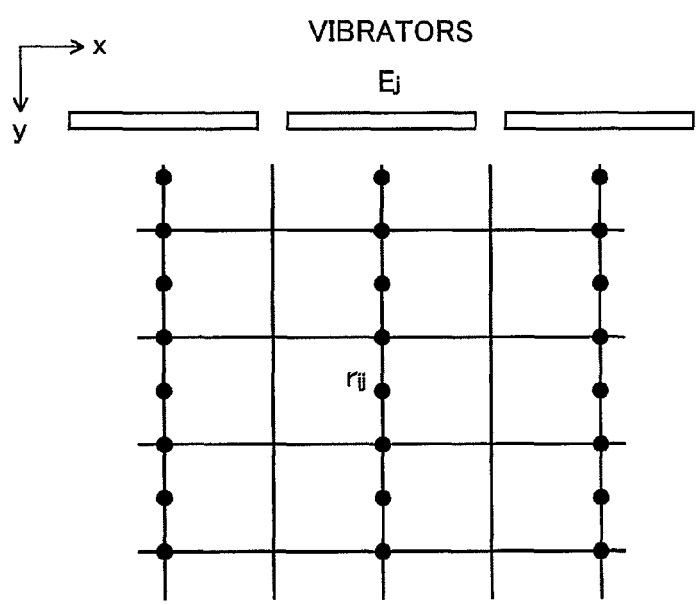
FIG. 9 shows a relationship between a group of arranged vibrators and sampling intervals of reception signals in the fourth embodiment of the present invention.

FIG. 9 shows a relationship between a group of arranged vibrators and sampling intervals of reception signals in the fourth embodiment of the present invention. FIG. 9 shows the case where the number of vibrators is a half of the azimuth resolving power, and may obtain reception sample data twice the axial resolving power (y direction). Note that, according to the sampling theorem, even when sampling is performed at the twice or more frequency relative to the maximum frequency of the reception signals, effective independent information is not obtained. Therefore, the inverse matrix $A^{-1}$ no longer exists. That is, the upper limit of the number of sample data according to the sampling theorem is the upper limit of resolving power of tomographic images to be obtained.

Next, the fifth embodiment of the present invention will be explained. In the fifth embodiment, tomographic image construction by superimposing partial transmissions is performed. The basic configuration of the ultrasonic imaging apparatus is the same as that of any one of the first to third embodiments.

For example, the sound source information calculating unit 55 shown in FIG. 1 calculates a product of the inverse matrix of the conversion matrix calculated by the inverse matrix calculating unit 54 and the reception signal matrix generated by the sampling unit 41 with respect to the respective regions formed by dividing the section of the object into plural regions.

Figure 10:
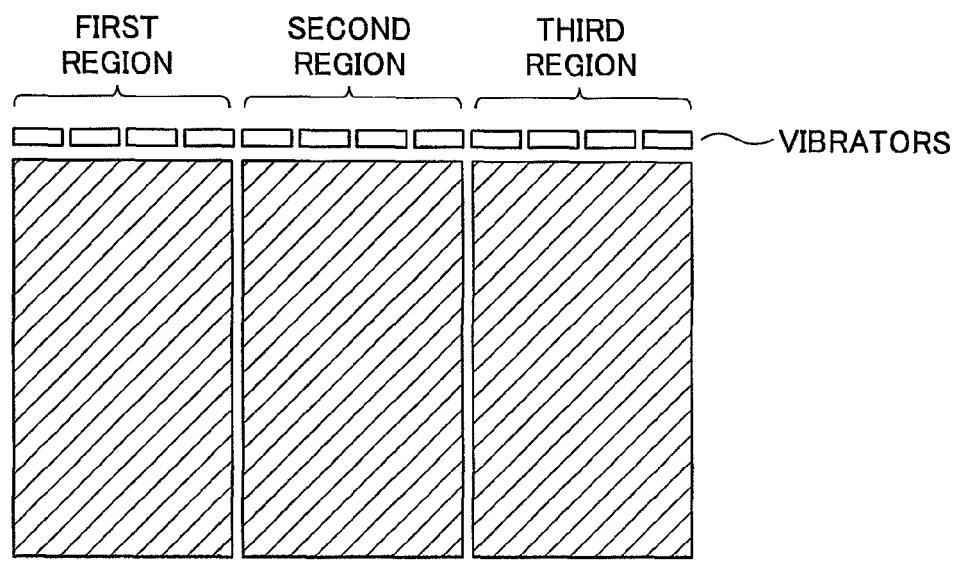
FIG. 10 shows an example of generating tomographic images by diving a section of the object into small regions.

FIG. 10 shows an example of generating tomographic images by diving a section of the object into small regions. The calculation of sound source information according to the present invention is to solve the simultaneous linear equations, and the calculation becomes complex as the amount of the section coordinate data is larger. Since m×n equations hold, the computation becomes simpler as the number of equations is smaller. That is, the calculation time is shorter in computation with respect to the entire section of the object at once than in computation with respect to plural divided relatively small regions. In this regard, the conversion matrix A in the simultaneous linear equations is the same if the geometric conditions of the divided regions are kept equal. Thus, not only the advance preparation of the calculation is saved, but also the computation algorithm can be simplified.

Next, the sixth embodiment of the present invention will be explained. In the sixth embodiment, tomographic image construction by superimposing partial transmissions is performed by formation of transmission focus and computation only on the regions of interest, and high-speed imaging and the improvement in S/N ratio can be realized. The basic configuration of the ultrasonic imaging apparatus is the same as that of any one of the first to third embodiments.

For example, the drive signal generating unit 20 shown in FIG. 1 supplies drive signals to the plural ultrasonic transducers 10a to form transmission focuses in the sectional regions sequentially selected within the object, and the sound source information calculating unit 55 calculates a product of the inverse matrix of the conversion matrix calculated by the inverse matrix calculating unit 54 and the reception signal matrix generated by the sampling unit 41 with respect to the sequentially selected sectional regions.

According to the present invention, tomographic images can be obtained by one transmission and reception, but it is difficult to generate sufficient sound pressure by one transmission and reception with respect to the whole space that spreads out in a fan-like form from the small ultrasonic aperture as in sector scan. Therefore, in the probe for sector, it is necessary to partially raise the sound pressure within the living body by controlling the ultrasonic beam direction under the same phase control as in the related art. In this case, tomographic images can be obtained from the inverse matrix $A^{-1}$ defined by the whole space, however, the S/N ratio becomes lower in the region at the low sound pressure and good images can not be obtained.

Figure 11:
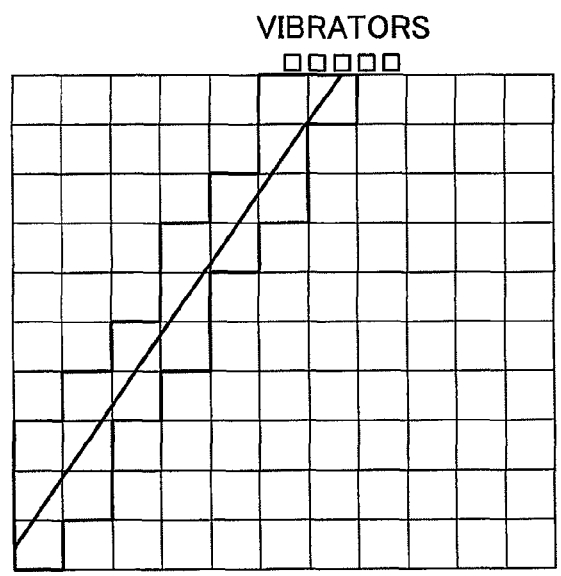
FIG. 11 shows an example of calculating sound source information by forming transmission focuses in the sequentially selected sectional regions.

Accordingly, as shown in FIG. 11, the calculation of sound source information S only in the region phase-controlled for obtaining sufficient S/N ratio is efficient because it takes the shorter calculation time. For the purpose, the transmission focuses are formed in the sectional regions sequentially selected within the object while the transmission direction is sequentially changed, and the region of the sound source information to be calculated is changed according to the transmission direction. By repeating the operation, the sound source information of the whole region of interest can be obtained. In the embodiment, the same method as in the related art is employed for transmission of ultrasonic waves, however, the resolving power is independent of the thickness and the influence of focal point of the ultrasonic beam in image construction, and the sufficient sound pressure within the object is intended for obtaining a good S/N ratio.

Next, the seventh embodiment of the present invention will be explained. In the seventh embodiment, the range of the condition for the point sound sources is extended by creating the conversion matrix and the inverse matrix in consideration of multiple reflection. The basic configuration of the ultrasonic imaging apparatus is the same as that of any one of the first to third embodiments.

On the surface of the vibrator, the received ultrasonic waves are largely reflected. Accordingly, the ultrasonic waves reaching the vibrator from the strong sound source located at the small distance from the vibrator are reflected on the surface of the vibrator and guided into the object again. If the ultrasonic waves reflected on the surface of the vibrator are ultrasonic waves generated from the strong sound source, it is expected that a strong reflection source is there and ultrasonic waves are reflected again by the reflection source again and travel toward the vibrator.

Figure 12:
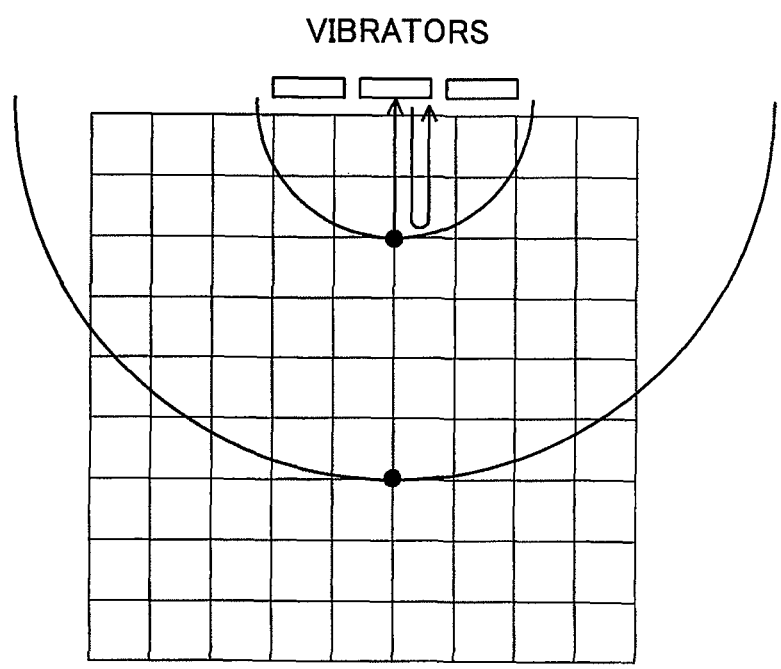
FIG. 12 shows a status that the ultrasonic waves multiply-reflected reach the vibrator.

FIG. 12 shows a status that the ultrasonic waves multiply-reflected reach the vibrator. The ultrasonic waves multiply-reflected by a strong reflection source are propagated and received at a distance three times the propagation distance of the original reception signal as shown in FIG. 12. This indicates the possibility that the sound source information at the depth i/3 is added to the reception signal at the depth i.

Accordingly, it is effective to add the reception signal from the depth i/3 as sound source information as a value in the conversion matrix A as expressed in the equations (11). For example, the conversion matrix calculating unit 53 calculates a conversion matrix on the assumption that sound source information at a depth i/3, which is one third of a certain depth i, is added to a reception signal from the certain depth i. How much the sound source information contributes is not completely determined, however, it is reasonable to multiply the intensity $r_{(i/3)j}$ of the reception signal from the depth i/3 by an appropriate coefficient "b".

If $(j-x)^2+y^2=i^2, a_{ij-yx}=w_{ij-yx}$

If $(j-x)^2+y^2=(i/3)^2, a_{ij-yx}=br_{(i/3)j-yx}$ (11)

Next, the eighth embodiment of the present invention will be explained. In the eighth embodiment, enlarged display is performed by changing the sampling period according to the enlargement factor and computing the limited part. The basic configuration of the ultrasonic imaging apparatus is the same as that of any one of the first to third embodiments.

For example, the sampling unit 41 as shown in FIG. 1 raises the sampling frequency of the reception signals processed by the reception signal processing unit 30, and thereby, the sound source information calculating unit 55 generates an image signal representing an enlarged ultrasonic image.

In the present invention, the number of simultaneous linear equations is given by m×n. That is, if the image display resolving power on the monitor is constant, the number is independent of the distance of the object on the tomographic surface. This means that the level of computation difficulty does not change even in scaling display. What is necessary is to keep the number of m×n even at scaling.

Figure 13:
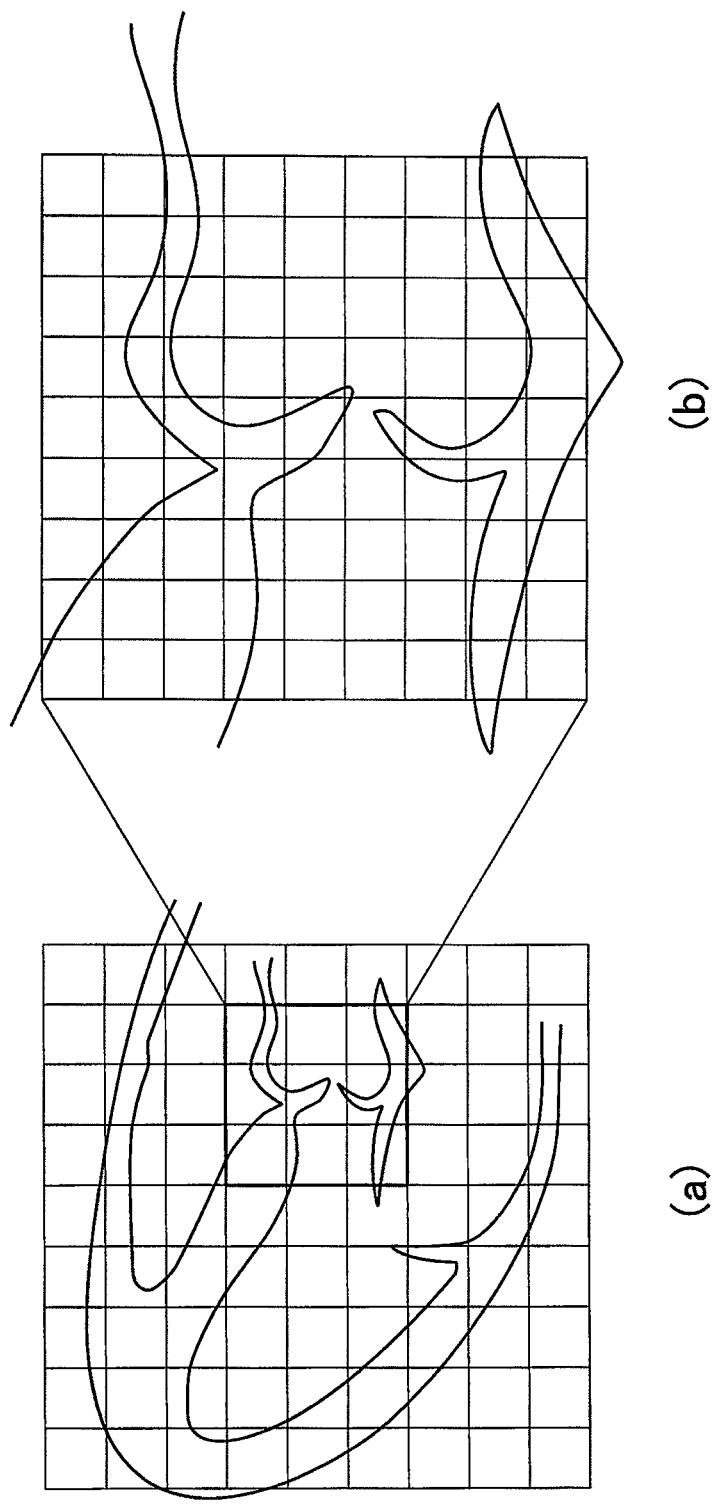
FIG. 13 shows an example of enlarged display.

FIG. 13 shows an example of enlarged display. Generally, when a part of the region shown in FIG. 13(a) is enlarged and displayed as shown in FIG. 13(b), the number of vibrators involved in reception is reduced and the time range of the reception signals as targets is also reduced. That is, although the number of data is reduced without change, the number of data can be secured by raising the sampling frequency.

How much the sampling frequency should be raised for securing the number of data also depends on the enlarging method, and can not be completely determined. How many times the sampling frequency is multiplied is determined to secure m×n data in the range of reception signals contributing to the sound source regions to be obtained. Note that there is no point in setting the sampling frequency to the maximum sampling frequency determined by the sampling theory, i.e., the Nyquist frequency. This is because that independent equations are not obtained from sampling at the Nyquist frequency or more, and the solution of the simultaneous linear equations is not obtained. Conversely, the range in which the m×n data are secured in sampling at the Nyquist frequency is the maximum enlargement factor.

Next, the ninth embodiment of the present invention will be explained. In the ninth embodiment, the temporal change in image information in an arbitrary direction is observed by computation of only the arbitrarily selected position. The basic configuration of the ultrasonic imaging apparatus is the same as that of any one of the first to third embodiments.

For example, the sound source information calculating unit 55 shown in FIG. 1 repeatedly calculates products of the inverse matrix of the conversion matrix calculated by the inverse matrix calculating unit 54 and the reception signal matrix generated by the sampling unit 41 with respect to the selected sectional regions, and thereby, generates an image signal representing the temporal change in image information in the selected sectional regions.

Figure 14:
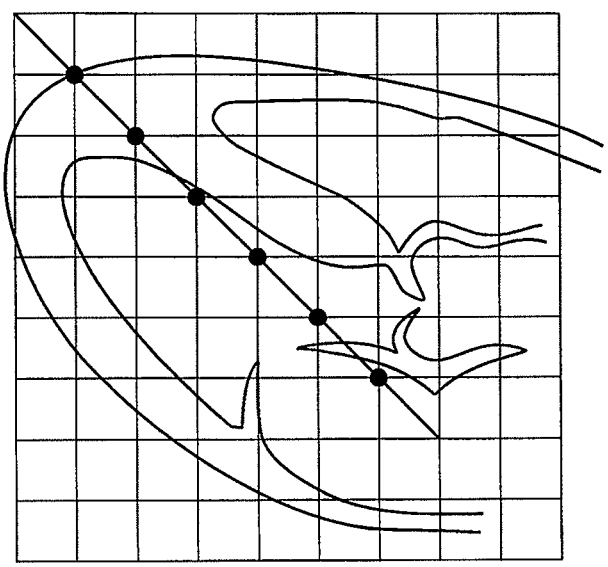
FIG. 14 shows an example of selecting image information in an arbitrary direction on a section.

FIG. 14 shows an example of selecting image information in an arbitrary direction on a section. In the solution method of the simultaneous linear equations using matrices, it is not necessary to simultaneously obtain all of the unknown values S. Only the desired $s_{yx}$ can be obtained. For example, obtaining the temporal change in image information in an arbitrary direction on a section is clinically effective. This is called an arbitrary direction M mode. In this regard, only the points shown in FIG. 14 may be selectively calculated and the number of computations becomes smaller. Since the arbitrary sound source information can selectively be calculated, the locations to be obtained are arbitrary and not necessary to be locations on a straight line. For example, in the case of the heart shown in FIG. 14, the change of heart muscle can be followed with the range along the heart muscle as a target of calculation.

Next, the tenth embodiment of the present invention will be explained. In the tenth embodiment, weighting on the point sound sources with widths is performed by calculating the inverse matrix in consideration of the size of the vibrator. The basic configuration of the ultrasonic imaging apparatus is the same as that of any one of the first to third embodiments.

For example, the conversion matrix calculating unit 53 shown in FIG. 1 calculates a conversion matrix on the assumption that, to a reception signal from a certain depth i, a reception signal received with a time difference corresponding to the width of each ultrasonic transducer (vibrator) 10a is added.

Figure 15:
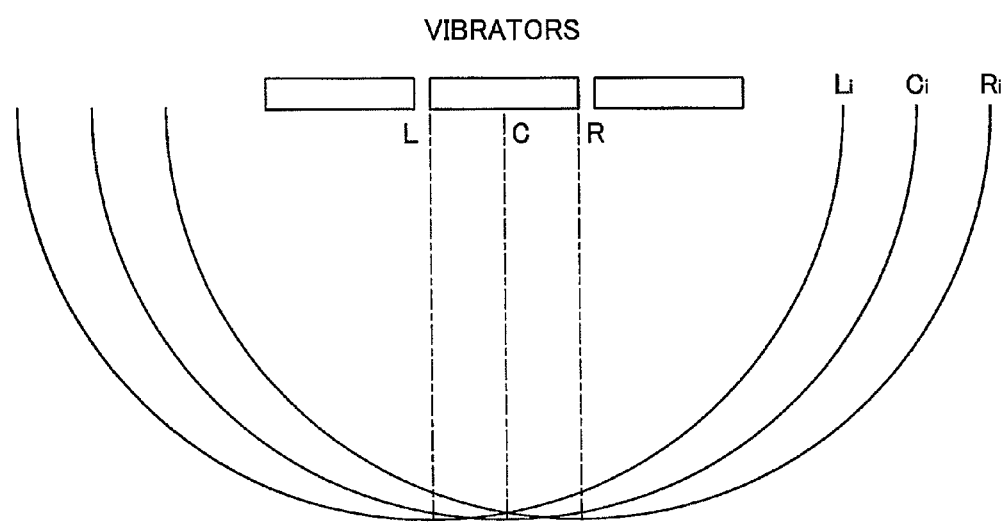
FIG. 15 shows reflection waves generated by reflection of ultrasonic waves transmitted from plural vibrators within the object.

FIG. 15 shows reflection waves generated by reflection of ultrasonic waves transmitted from plural vibrators within the object. Since the vibrator has a certain level of size, the signal received by one vibrator at the same time is the summation of reflection waves from spaces corresponding to the vibrators in size as shown in FIG. 15. At the time corresponding to the depth i, the signal received by the central part C of the vibrator is reflection waves from points on concentric circles having a radius of "i" around the vibrator center.

At the end L or R of the vibrator, the points on the concentric circles having a radius of "i" around the end should be considered, and this spreads out to a considerable angle at the left end L and the right end R. As a whole, the reflection waves from the regions surrounded by arc $L_i$ and arc $R_i$, and arc $C_i$ depending on the location are received at the same time. In calculation of the conversion matrix A, as expressed in the equation (12), the sound source information can be estimated more accurately in consideration of the vibrator width.

$$\text{If } (j+H-x)^2+y^2=i^2 \sim (j-H-x)^2+y^2=i^2, a_{ij-yx}=w_{ij-yx} \tag{12}$$

where H indicates the width of the vibrator.

Next, the eleventh embodiment of the present invention will be explained. In the eleventh embodiment, the scale of the transmission circuit (pulser or the like) is reduced by supplying a single drive signal to plural vibrators. The basic configuration of the ultrasonic imaging apparatus is the same as that of any one of the first to third embodiments.

Figure 16:
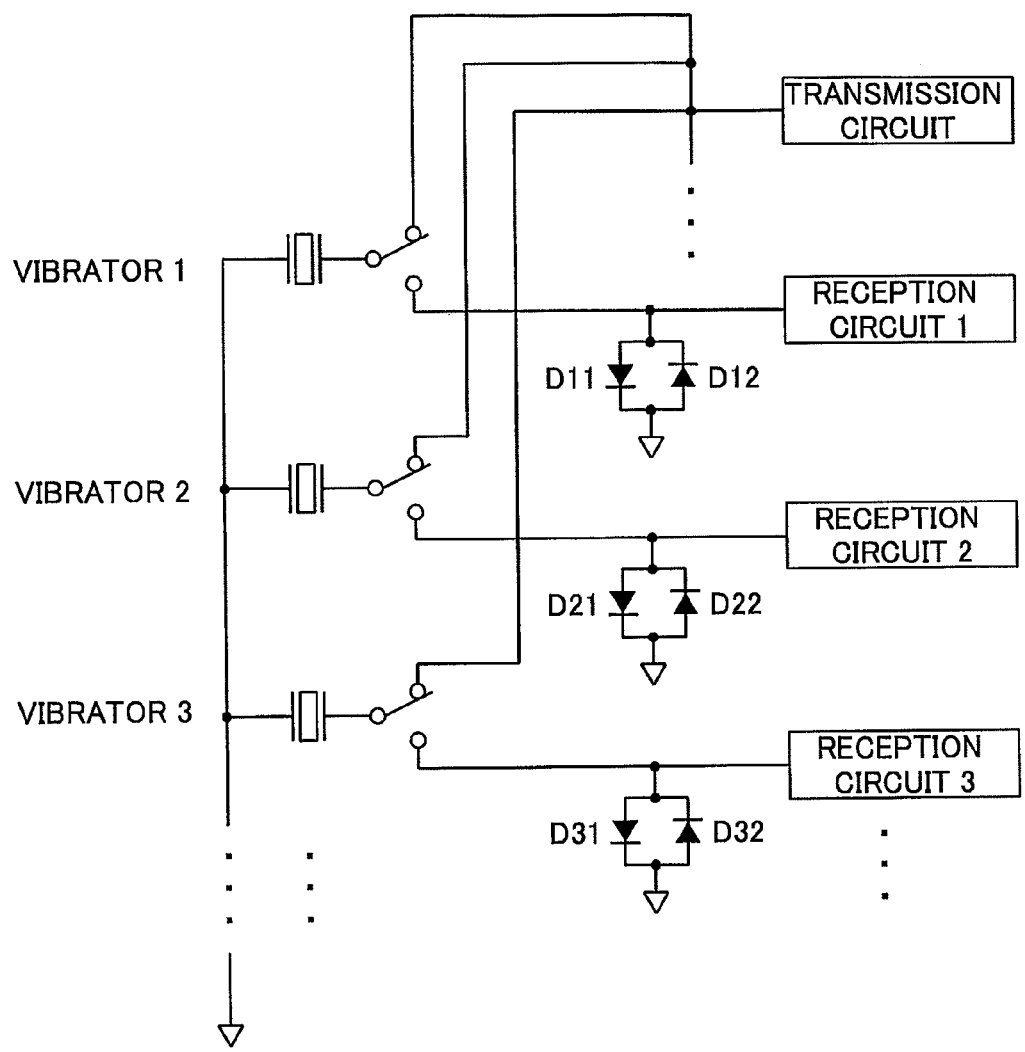
FIG. 16 shows a part of the transmitting and receiving unit of an ultrasonic imaging apparatus according to the eleventh embodiment of the present invention.

FIG. 16 shows a part of the transmitting and receiving unit of an ultrasonic imaging apparatus according to the eleventh embodiment of the present invention. In the present invention, it is not necessarily required to phase-control the transmitted ultrasonic beam. Accordingly, the drive signals may have the same phase and the same waveform with respect to the plural vibrators. In reception, it is necessary to obtain the reception signals with respect to each of the plural vibrators.

For the purpose, as shown in FIG. 16, the common drive signal is supplied to the plural vibrators using the common transmission circuit (pulser or the like) in the drive signal generating unit, and only reception circuits (preamplifiers or the like) may be provided with respect to each of the plural vibrators. Generally, the reception signal is an extremely weak voltage, while the drive signal is a sufficiently large voltage. Therefore, in the reception system circuit, the plural vibrators and the reference potential (the ground potential in the embodiment) are connected via diodes D11 and D12 parallel-connected in the opposite directions and so on, and thus, the large voltage passes through the diodes D11 and D12 and so on and the reception signal of the weak voltage is inputted to the reception circuit. According to the embodiment, the number of transmission circuits can be reduced and the transmission phase control circuit is no longer necessary, and the circuit scale can greatly be reduced.

Next, the twelfth embodiment of the present invention will be explained. In the twelfth embodiment, spherical waves are formed by synthesizing ultrasonic waves transmitted from plural vibrators. The basic configuration of the ultrasonic imaging apparatus is the same as that of any one of the first to third embodiments.

Figure 17:
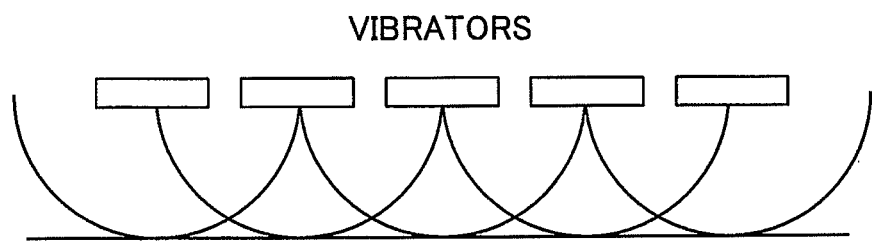
FIG. 17 shows synthesis of ultrasonic waves transmitted from plural vibrators.

FIG. 17 shows synthesis of ultrasonic waves transmitted from plural vibrators. According to the present invention, as has been described in the eleventh embodiment, a drive signal can be commonly used with respect to the plural vibrators. In transmission with the common drive signal, even the arranged vibrators behave as if they are a large flat vibrator, and form planar waves as a transmission acoustic field as shown in FIG. 17. This is not problematic in linear scan or convex scan, however, in sector scan in which the region other than the region immediately under the vibrator is set as a region of interest, it is problematic that the wavefront waves can not be formed.

Figure 18:
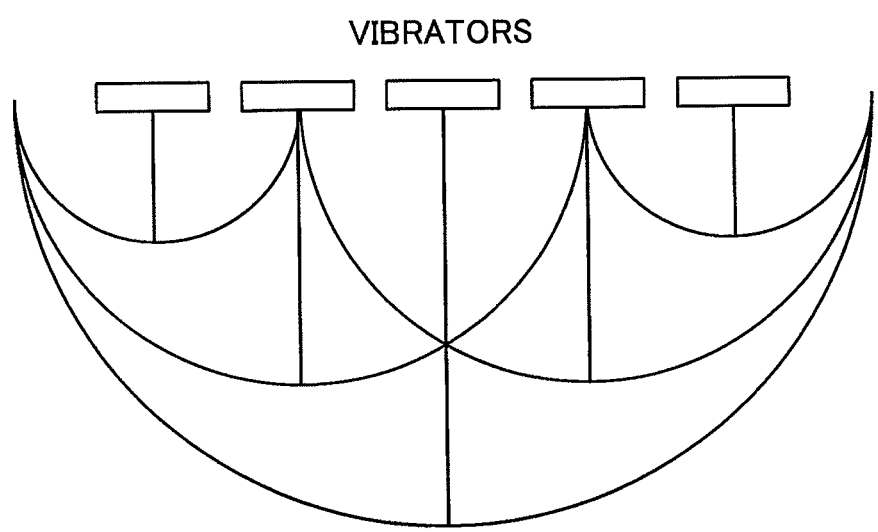
FIG. 18 shows an example of providing delays to the drive signals with respect to the vibrators on both ends.

Accordingly, as shown in FIG. 18, delays are provided to the drive signals with respect to the vibrators on both ends of the central vibrator such that the transmission acoustic field becomes an acoustic field from the point sound source. In this regard, assuming that the aperture of the vibrator is sufficiently small, if the wavefront under the vibrator is neglected and the region of interest is considered only on the wavefront spreading toward the both ends, the amounts of delay provided to the drive signals may be fixed amounts determined by the arrangement position of the vibrator.

Figure 19:
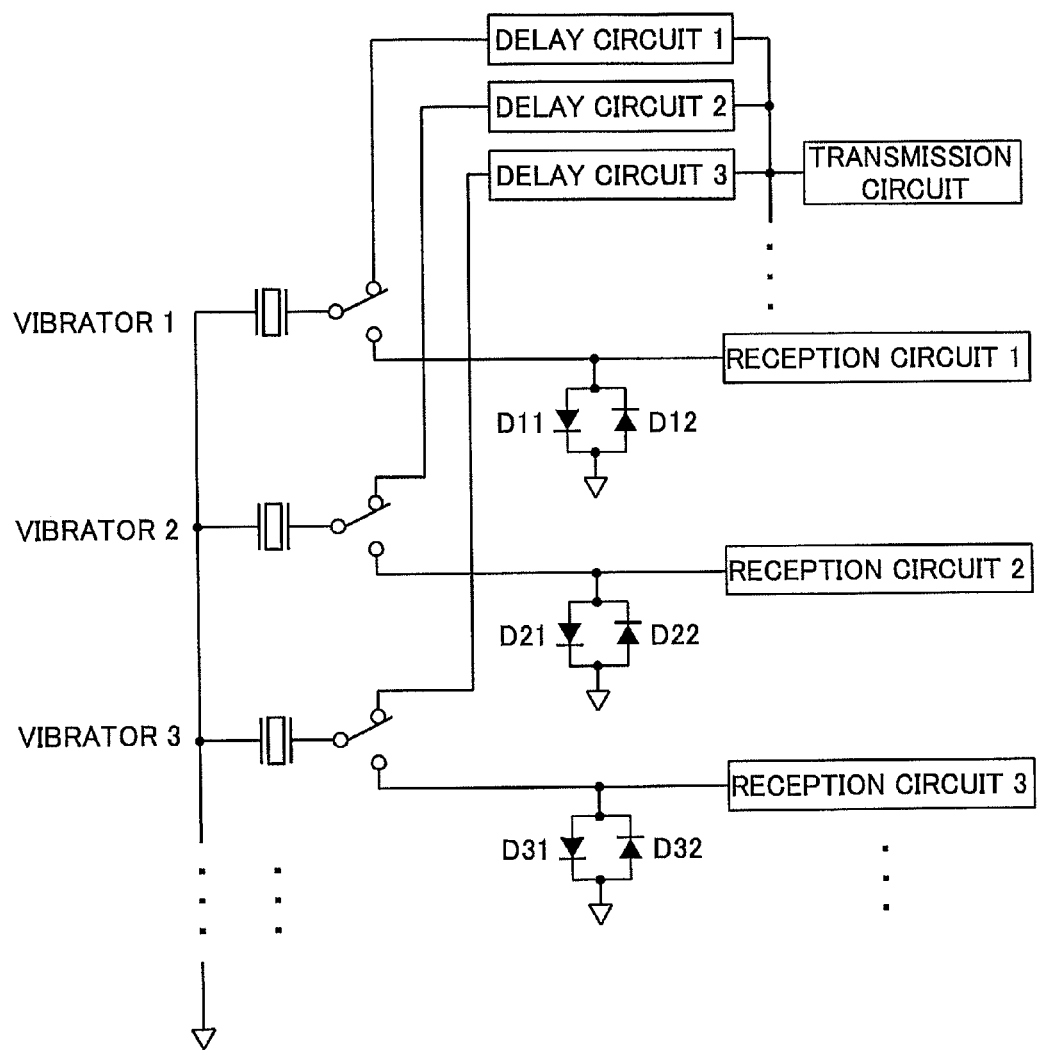
FIG. 19 shows a part of the transmitting and receiving unit of an ultrasonic imaging apparatus according to the twelfth embodiment of the present invention.
Figure 20:
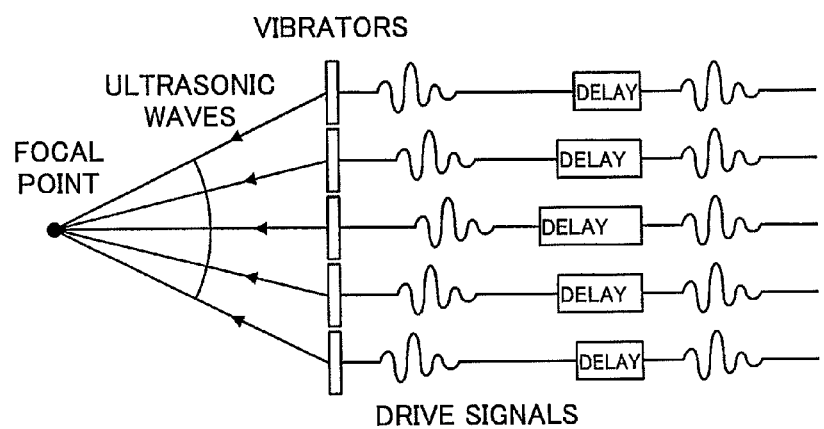
FIG. 20 is a diagram for explanation of transmission beam forming.
Figure 21:
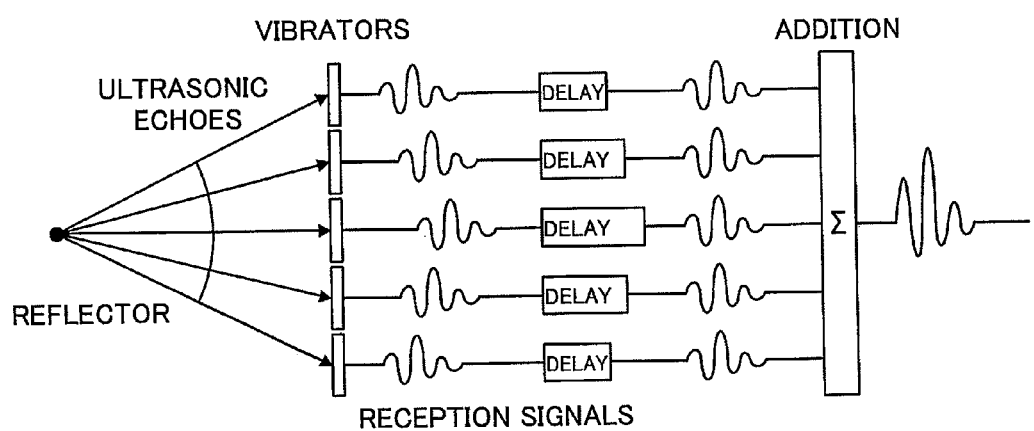
FIG. 21 is a diagram for explanation of reception beam forming.
Figure 22:
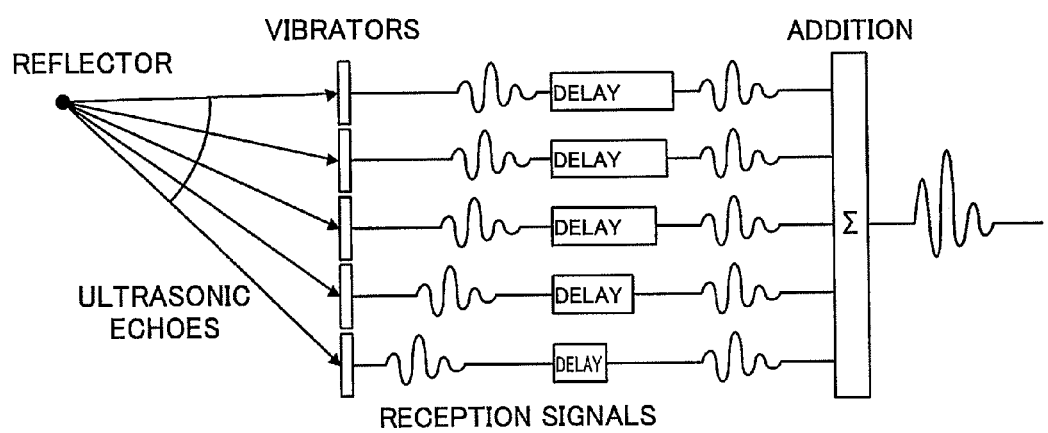
FIG. 22 shows an example of tilting an ultrasonic beam.
Figure 23:
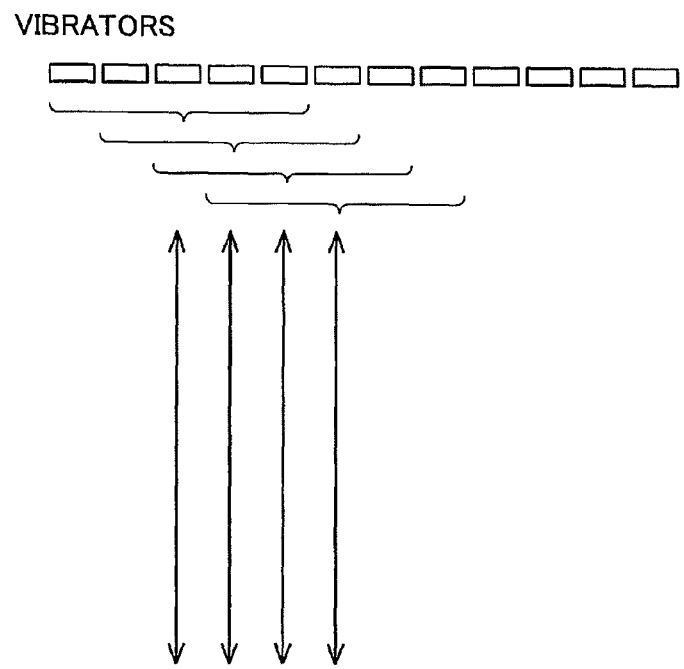
FIG. 23 shows shifting of an ultrasonic beam in the case of linear scan.
Figure 24:
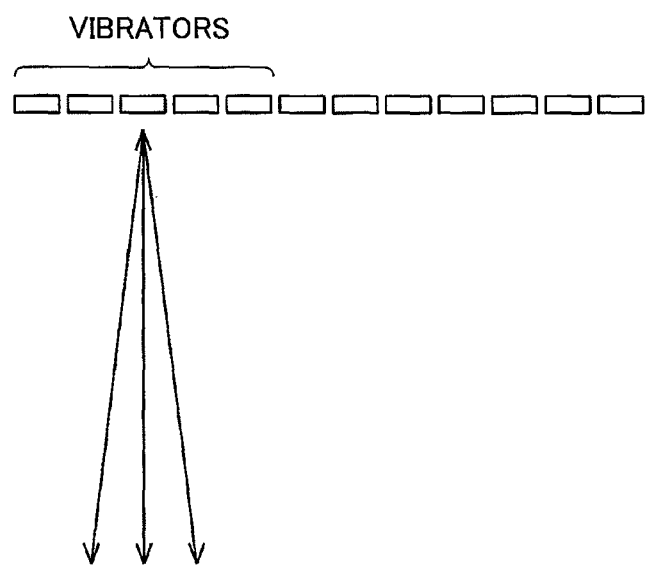
FIG. 24 is a diagram for explanation of a micro-angle method.
Figure 25:
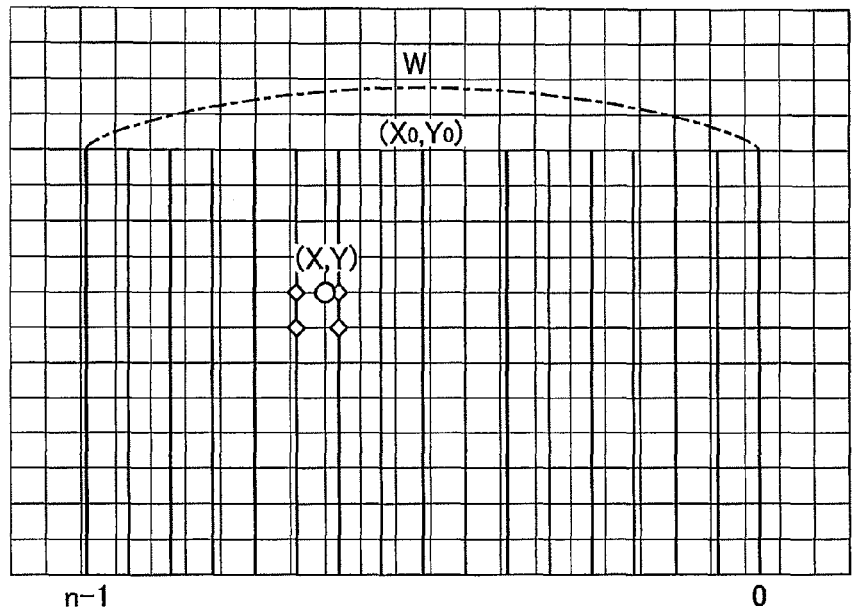
FIG. 25 shows an example of scan conversion in the case of linear scan.
Figure 26:
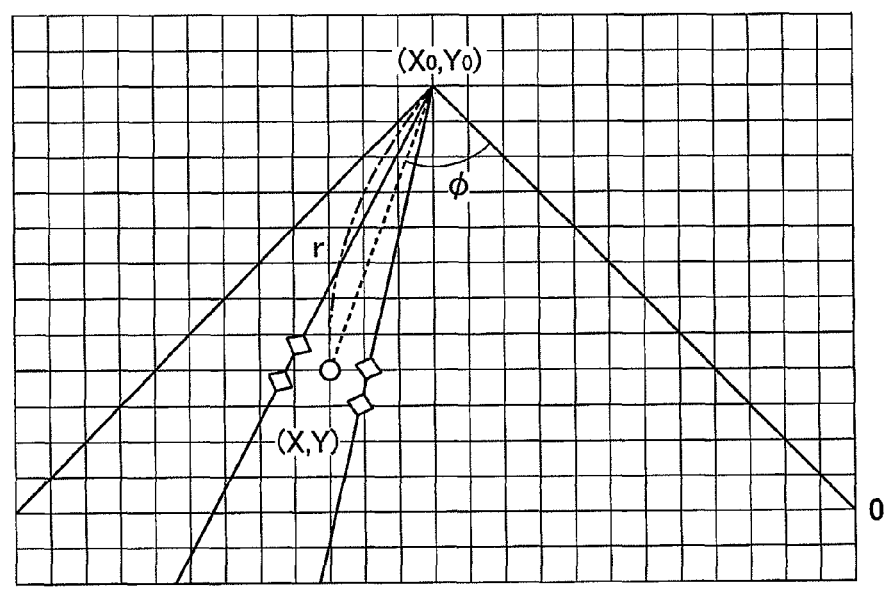
FIG. 26 shows an example of scan conversion in the case of sector scan.

FIG. 19 shows a part of the transmitting and receiving unit of an ultrasonic imaging apparatus according to the twelfth embodiment of the present invention. As shown in FIG. 19, the plural vibrators and the transmission circuit are connected via the respective delay circuits. Thereby, fixed amounts of delay are provided to the drive signals respectively supplied to the plural vibrators, and the ultrasonic waves transmitted to the plural vibrators form a spherical wave. The rest is the same as that of the eleventh embodiment shown in FIG. 16.

According to the above explained embodiments, tomographic images can be obtained by one transmission and reception. Further, the method of generating images does not depend on the sound speed information, and thus, the images do not change depending on the sound speed setting. In the scan conversion, the conversion method and interpolation method should be set with respect to each shape of the ultrasonic probe, however, according to these embodiments, the inverse matrix is obtained in advance and the tomographic images can be obtained by exactly the same calculation. It is not necessary to focus the ultrasonic waves at transmission, and thus, there is no need to provide individual drive signals to the individual vibrators and the transmission circuit can be simplified. Further, in principle, 3D volume information can be calculated. Furthermore, in the case of computation in the complex region, Doppler tomographic images can be obtained at two transmission and reception in principle.

The invention claimed is:

1. An ultrasonic imaging apparatus comprising:
   a transmitter configured to supply at least one drive signal to at least one ultrasonic transducer to transmit ultrasonic waves to an object to be inspected;
   a receiver configured to process reception signals outputted from plural ultrasonic transducers receiving ultrasonic echoes from the object; and
   a central processing unit comprising:
      a sampling unit configured to sample the reception signals processed by said receiver to generate a reception signal matrix representing reception signals obtained by receiving ultrasonic echoes from plural sampling points on a section of the object with respect to said plural ultrasonic transducers and depths of the plural sampling points;
      a conversion matrix calculating unit configured to calculate a conversion matrix representing weighting information when ultrasonic echoes from the plural sampling points are synthesized to cause reception signals of said plural ultrasonic transducers, said conversion matrix being calculated in consideration of a width of each of said plural ultrasonic transducers such that each of said plural ultrasonic transducers receives the ultrasonic echoes at the same time from sampling points within a region surrounded by circular arcs having the same radius around center points which are located in a reception area from one end to the other end of said ultrasonic transducer;
      an inverse matrix calculating unit configured to calculate an inverse matrix of the conversion matrix calculated by said conversion matrix calculating unit; and
      a sound source information calculating unit configured to calculate a product of the inverse matrix calculated by said inverse matrix calculating unit and the reception signal matrix generated by said sampling unit to obtain a sound source signal matrix representing information on reflective sound sources at the plural sampling points within the object, and generate an image signal representing an ultrasonic image within the object, based on the sound source signal matrix.

2. The ultrasonic imaging apparatus according to claim 1, wherein said receiver includes plural anti-aliasing filters configured to perform filter processing to prevent aliasing in sampling the reception signals, respectively.

3. The ultrasonic imaging apparatus according to claim 1, wherein said sampling unit is configured to sample reception signals obtained based on ultrasonic echoes received by said plural ultrasonic transducers at plural time points.

4. The ultrasonic imaging apparatus according to claim 1, wherein said conversion matrix calculating unit is configured to calculate the conversion matrix when ultrasonic echoes from plural sampling points two-dimensionally arranged on the section of the object are synthesized.

5. The ultrasonic imaging apparatus according to claim 1, wherein the central processing unit further comprises:
a weighting processing unit configured to weight plural elements included in the conversion matrix calculated by said conversion matrix calculating unit, based on acoustic field estimation;
wherein said inverse matrix calculating unit is configured to calculate the inverse matrix of the conversion matrix weighted by said weighting processing unit.

6. The ultrasonic imaging apparatus according to claim 1, wherein:
said receiver includes plural quadrature detectors configured to perform quadrature detection processing on the reception signals to obtain real parts and imaginary parts of the reception signals;
said sampling unit includes a first sampling unit configured to sample the real parts of the reception signals to generate a first reception signal matrix representing real parts of the reception signals obtained by receiving the ultrasonic echoes from the plural sampling points on the section of the object, and a second sampling unit configured to sample the imaginary parts of the reception signals to generate a second reception signal matrix representing imaginary parts of the reception signals obtained by receiving the ultrasonic echoes from the plural sampling points on the section of the object;
said sound source information calculating unit includes a first sound source information calculating unit configured to calculate a product of the inverse matrix calculated by said inverse matrix calculating unit and the first reception signal matrix generated by said first sampling unit to obtain a first sound source signal matrix representing information on the reflective sound sources within the object, and a second sound source information calculating unit configured to calculate a product of the inverse matrix calculated by said inverse matrix calculating unit and the second reception signal matrix generated by said second sampling unit to obtain a second sound source signal matrix representing information on the reflective sound sources within the object; and
the central processing unit further comprises an amplitude computing unit configured to obtain amplitudes of sound source signals based on real parts of the sound source signals included in the first sound source signal matrix and imaginary parts of the sound source signals included in the second sound source signal matrix, and generate an image signal representing an ultrasonic image within the object, based on the amplitudes of the sound source signals.

7. The ultrasonic imaging apparatus according to claim 1, wherein said sound source information calculating unit is configured to calculate a product of the inverse matrix calculated by said inverse matrix calculating unit and the reception signal matrix generated by said sampling unit with respect to each region formed by dividing the section of the object into plural regions.

8. The ultrasonic imaging apparatus according to claim 1, wherein said transmitter is configured to supply drive signals to the plural ultrasonic transducers, respectively, so as to form transmission focuses on sectional regions sequentially selected within the object; and
said sound source information calculating unit is configured to calculate a product of the inverse matrix calculated by said inverse matrix calculating unit and the reception signal matrix generated by said sampling unit with respect to the sequentially selected sectional regions.

9. The ultrasonic imaging apparatus according to claim 1, wherein said conversion matrix calculating unit is configured to calculate the conversion matrix on an assumption that a reception signal outputted from respective one of said ultrasonic transducers receiving an ultrasonic echo from a sampling point at a first distance from said ultrasonic transducer includes a signal component caused by an ultrasonic echo multiple-reflected between said ultrasonic transducer and another sampling point at a second distance that is one third of the first distance from said ultrasonic transducer.

10. The ultrasonic imaging apparatus according to claim 1, wherein said sampling unit is configured to raise a sampling frequency of the reception signals processed by said receiver, and said sound source information calculating unit is configured to generate an image signal representing an enlarged ultrasonic image based on the sound source signal matrix representing the reception signals sampled with the raised sampling frequency.

11. The ultrasonic imaging apparatus according to claim 1, wherein said sound source information calculating unit is configured to repeatedly calculate products of the inverse matrix calculated by said inverse matrix calculating unit and the reception signal matrix generated by said sampling unit with respect to selected sectional regions, and thereby, generate an image signal representing temporal change of image information in the selected sectional regions.

12. The ultrasonic imaging apparatus according to claim 1, wherein said transmitter includes a transmission circuit configured to supply a common drive signal to plural ultrasonic transducers.

13. The ultrasonic imaging apparatus according to claim 1, wherein said transmitter includes plural delay circuits configured to provide unique delay times to plural ultrasonic transducers, respectively, and a transmission circuit configured to supply drive signals to said plural ultrasonic transducers via said plural delay circuits, respectively.

14. An ultrasonic imaging method to be used in an ultrasonic imaging apparatus having plural ultrasonic transducers, said method comprising the steps of:
(a) calculating, using a central processing unit provided in said ultrasonic imaging apparatus, a conversion matrix representing weighting information when ultrasonic echoes from plural sampling points on a section of an object to be inspected are synthesized to cause reception signals of said plural ultrasonic transducers, said conversion matrix being calculated in consideration of a width of each of said plural ultrasonic transducers such that each of said plural ultrasonic transducers receives the ultrasonic echoes at the same time from sampling points within a region surrounded by circular arcs having the same radius around center points which are located in a reception area from one end to the other end of said ultrasonic transducer;

(b) calculating, using said central processing unit, an inverse matrix of the conversion matrix calculated at step (a);

(c) supplying, using a drive signal generating unit provided in said ultrasonic imaging apparatus, at least one drive signal to at least one ultrasonic transducer to transmit ultrasonic waves to the object;

(d) processing, using a reception signal processing unit provided in said ultrasonic imaging apparatus, reception signals outputted from plural ultrasonic transducers receiving ultrasonic echoes from the object;

(e) sampling, using a sampling unit provided in said ultrasonic imaging apparatus, the reception signals processed at step (d) to generate a reception signal matrix representing reception signals obtained by receiving ultrasonic echoes from the plural sampling points with respect to said plural ultrasonic transducers and depths of the plural sampling points; and (f) calculating, using said central processing unit, a product of the inverse matrix calculated at step (b) and the reception signal matrix generated at step (e) to obtain a sound source signal matrix representing information on reflective sound sources at the plural sampling points within the object, and generating an image signal representing an ultrasonic image within the object, based on the sound source signal matrix.

\* \* \* \* \*